(12) United States Patent
Fry et al.

(10) Patent No.: US 10,584,146 B2
(45) Date of Patent: Mar. 10, 2020

(54) HEME PEPTIDE MATERIALS FOR ANTI-INFLAMMATORY REGENERATIVE NANOBIOMEDICINE

(71) Applicant: UCHICAGO ARGONNE, LLC, Chicago, IL (US)

(72) Inventors: Harry C. Fry, Lincolnwood, IL (US); Lee A. Solomon, Chicago, IL (US)

(73) Assignee: UChicago Argonne, LLC, Chicago, IL (US)

( * ) Notice: Subject to any disclaimer, the term of this patent is extended or adjusted under 35 U.S.C. 154(b) by 0 days.

(21) Appl. No.: 15/833,978

(22) Filed: Dec. 6, 2017

(65) Prior Publication Data
US 2018/0244723 A1 Aug. 30, 2018

Related U.S. Application Data

(60) Provisional application No. 62/431,119, filed on Dec. 7, 2016.

(51) Int. Cl.
*C07K 7/08* (2006.01)
*C07K 7/06* (2006.01)
(Continued)

(52) U.S. Cl.
CPC .................. *C07K 7/08* (2013.01); *A61K 9/70* (2013.01); *A61K 47/542* (2017.08); *A61P 9/00* (2018.01);
(Continued)

(58) Field of Classification Search
CPC .... A61K 31/215; A61K 9/0026; A61K 31/19; A61K 38/42; C12N 2830/002; C07K 14/47; C07K 7/06
See application file for complete search history.

(56) References Cited

U.S. PATENT DOCUMENTS 8,580,923 B2 11/2013 Stupp et al.
2016/0090583 A1 3/2016 Super et al.

FOREIGN PATENT DOCUMENTS

WO  WO-2006/096614 A2  9/2006

OTHER PUBLICATIONS

Fry et al. Photoinitiated charge separation in a hybrid titanium dioxide metalloporphyrin peptide material. Nat Commun. Aug. 18, 2014; 5: 4606. (Year: 2014).*
(Continued)

*Primary Examiner* — Soren Harward
*Assistant Examiner* — Jia-Hai Lee
(74) *Attorney, Agent, or Firm* — Foley & Lardner LLP

(57) ABSTRACT

Heme released as a result of sustained injury leads to toxicity and triggers an inflammatory response and tissue damage. Heme oxygenase, an enzyme, recognizes, binds free heme and breaks it down as a part of the anti-inflammatory response. The present disclosure relates to a class of peptide amphiphiles that mimic the heme oxygenase function, and have shown that the designed peptide is able to bind and break down heme thus validating its potential as an anti-inflammatory agent that promotes tissue repair and useful in wound healing. The disclosed peptide sequence design provides control of amphiphile peptides' supramolecular structure and function. Applicants have shown that the incorporated heme molecule can transport CO, which suggests that the peptides can also transport NO, $O_2$ and reactive oxygens, the molecules which are responsible for vasodilation, neurotransmission and cell death. Besides heme oxygenase function, it is believed that the designed peptides can recognize normal tissue adjacent to the damaged area and the peptide can self-assemble into fibers that promote healthy cell growth.

17 Claims, 31 Drawing Sheets
Specification includes a Sequence Listing.

(51) Int. Cl.
  C07K 5/11    (2006.01)
  A61P 9/00    (2006.01)
  A61K 9/70    (2006.01)
  A61P 29/00   (2006.01)
  A61K 47/54   (2017.01)
  A61K 38/00   (2006.01)
(52) U.S. Cl.
  CPC ............ *A61P 29/00* (2018.01); *C07K 5/1019* (2013.01); *C07K 7/06* (2013.01); *A61K 38/00* (2013.01); *C07K 2319/01* (2013.01)

(56) References Cited

OTHER PUBLICATIONS

Lim et al. Freeze drying of peptide drugs self-associated with long-circulating, biocompatible and biodegradable sterically stabilized phospholipid nanomicelles. International Journal of Pharmaceutics 356 (2008) 345-350. (Year: 2008).*
Balakrishnan, et al., "His26 Protonation in Cytochrome c Triggers Microsecond beta-Sheet Formation and Heme Exposure: Implications for Apoptosis," Journal of the American Chemical Society 134(46), pp. 19061-1969 (2012).
Baldwin & Chothia, "Hemoglobin—structural changes related to ligand and its allosteric mechanism," Journal of Molecular Biology 129(2), pp. 175-200 (1979).
Battistuzzi, et al., "Control of cytochrome c redox potential: Axial ligation and protein environment effects," Journal of the American Chemical Society 124(19), pp. 5315-5324 (2002).
Berghuis & Brayer, et al,. "Oxidation state dependent conformational changes in cytochrome-c," Journal of Molecular Biology 223(4), pp. 959-976 (1992).
Brown, et al., "Aggregation of ferrihaems. Dimerization and protolytic equilibria of protoferrihaem and deuteroferrihaem in aqueous solution," Biochemical Journal 117(4), pp. 733-739 (1970).
Bury, et al., "The promotion of functional urinary bladder regeneration using anti-inflammatory nanofibers," Biomaterials 35(34), pp. 9311-9321 (2014).
Chen & Rosi, "Peptide-Based Methods for the Preparation of Nanostructured Inorganic Materials," Angewandte Chemie 49(11), pp. 1924-1942 (2010).
Cosby, et al., "Nitrite reduction to nitric oxide by deoxyhemoglobin vasodilates the human circulation," Nature Medicine 9, pp. 1498-1505 (2003).
Cui, et al., "Self-Assembly of Peptide Amphiphiles: From Molecules to Nanostructures to Biomaterials," Peptides in Materials Science 94(1), pp. 1-18 (2010).
Dawson & Snyder, "Gases as biological messengers: nitric oxide and carbon monoxide in the brain," Journal of Neuroscience 14(9), pp. 5147-5159 (1994).
Escuder, et al., "Supramolecular gels as active media for organic reactions and catalysis," New Journal of Chemistry 43, pp. 1044-1054 (2010).
Fago, et al., "Allosteric regulation and temperature dependence of oxygen binding in human neuroglobin and cytoglobin—Molecular mechanisms and physiological significance," Journal of Biological Chemistry 279, pp. 44417-44426 (2004).
Fry, et al., "Photoinitated charge separation in a hybrid titanium dioxide metalloporphyrin peptide material," Nature Communications 5, 4606, 9 pages (2014).
Fry, et al., "Self-Assembly of Highly Ordered Peptide Amphiphile Metalloporphyrin Arrays," Journal of the American Chemical Society 134(36), pp. 14646-14649 (2012).
Ghanaati, et al., "Dynamic in vivo biocompatibility of angiogenic peptide amphiphile nanofibers," Biomaterials 30(31), pp. 6202-6212 (2009).

Ghirlanda, et al., "De novo design of a D-2-symmetrical protein that reproduces the diheme four-helix bundle in cytochrome bc1," Journal of the American Chemical Society 126(26), pp. 8141-8147 (2004).
Gibney, et al., "Self-assembly of heme A and heme B in a designed four-helix bundle: Implications for a cytochrome c oxidase maquette," Biochemistry 39(36), pp. 11041-11049 (2000).
Giordano, et al., "Biophysical Characterisation of Neuroglobin of the Icefish, a Natural Knockout for Hemoglobin and Myoglobin," PLoS ONE 7(12), pp. (2012).
Gozzelino, et al., "Mechanisms of Cell Protection by Heme Oxygenase-1," Annual Review of Pharmacology and Toxicology 50, pp. 323-354 (2010).
Grosset, et al., "Proof of principle in a de novo designed protein maquette: An allosterically regulated, charge-activated conformational switch in a tetra-alpha-helix bundle," Biochemistry 40(18), pp. 5474-5487 (2001).
Guler & Stupp, "A self-assembled nanofiber catalyst for ester hydrolysis," Journal of the American Chemical Society 129(40), pp. 12082-1208 (2007).
Hartgerink, et al., "Self-assembly and mineralization of peptide-amphipnile nanofibers," Science 294(5547), pp. 1684-1688 (2001).
Hersleth, et al., "Structures of the high-valent metal-ion haem-oxygen intermediates in peroxidases, oxygenases and catalases," Journal of Inorganic Biochemistry 100(4), pp. 460-476 (2006).
Hill, et al., "Self-Assembly: From Amphiphiles to Chromophores and Beyond," Molecules 19(6), pp. 8589-8609 (2014).
Ikeda-Saito, et al., "Coordination structure of the ferric heme iron in engineered distal histidine myoglobin mutants," Journal of Biological Chemistry 267, pp. 22843-22852 (1992).
Jiang & Wang, "Cytochrome C-mediated apoptosis," Annual Review of Biochemistry 73, pp. 87-106 (2004).
Josephy, et al., "The horeseradish peroxidase-catalyzed oxidation of 3,5,3',5'-tetramethylbenzidine—free-radical charge-transfer complex inetermediates," Journal of Biological Chemistry 257, pp. 3669-3675 (1982).
Kim, et al., "Beta-Sheet-Forming, Self-Assembled Peptide Nanomaterials towards Optical, Energy, and Healthcare Applications," Small 11(30), pp. 3623-3640 (2015).
Klassen, et al., "H2O2 determination by the I3(−) method and by KMnO4 titration," Analytical Chemistry 66(18), pp. 2921-2925 (1994).
Kluck, et al,. "The release of cytochrome c from mitochondria: A primary site for Bcl-2 regulation of apoptosis," Science 275(5303), pp. 1132-1136 (1997).
Koder, et al., "Design and engineering of an O-2 transport protein," Nature 458, pp. 305-309 (2009).
Kong & Yu, "Fourier transform infrared spectroscopic analysis of protein secondary structures," Acta Biochimica et Biophysica Sinica 39(8), pp. 549-559 (2007).
Korendovych, et al,. "Design of a switchable eliminase," Proceedings of the National Academy of Sciences USA 108(17), pp. 6823-6827 (2011).
Lakkisto, et al., "Expression of heme oxygenase-1 in response to myocardial infarction in rats," Journal of Molecular and Cellular Cardiology 34(10), pp. 1357-1365 (2002).
Manning, et al., "Circular dichroism studies of distorted alpha-helices, twisted beta-sheets, and beta-turns," Biophysical Chemistry 31(1-2), pp. 77-86 (1988).
Matson, et al., "Peptide self-assembly for crafting functional biological materials," Current Opinion in Solid State and Materials Science 15, pp. 225-235 (2011).
Moffet, et al., "Midpoint reduction potentials and heme binding stoichiometries of de novo proteins from designed combinatorial libraries," Biophysical Chemistry 105(2-3), pp. 231-239 (2003).
Newcomb, et al., "The Role of Nanoscale Architecture in Supramolecular Templating of Biomimetic Hydroxyapatite Mineralization," Small 8(14), pp. 2195-2202 (2012).
Nistor, et al., "EPR-spectroscopic evidence of a dominant His-Fe-III-His coordination in ferric neuroglobin," Chemical Physics Letters 361(5-6), pp. 355-361 (2002).

(56) References Cited

OTHER PUBLICATIONS

Petros, et al., "Femtomolar Zn(II) affinity in a peptide-based ligand designed to model thiolate-rich metalloprotein active sites" Inorganic Chemistry 45(25), pp. 9941-9958 (2006).
Poulos, "Heme Enzyme Structure and Function," Chemical Reviews 114(7), pp. 3919-3962 (2014).
Reedy & Gibney, et al., "Heme protein assemblies," Chemical Reviews 104(2), pp. 617-650 (2004).
Ribeiro, et al., "Reversible binding of nitric-oxide by a salivary heme protein from a bloodsucking insect," Science 260(5107), pp. 539-541 (1993).
Ryter, et al., "Heme oxygenase-1/carbon monoxide: From basic science to therapeutic applications," Physiological Reviews 86(2), pp. 583-650 (2006).
Shack & Clark, "Metalloporphyrins VI. Cycles of Changes in Systems Containing Heme," Journal of Biological Chemistry 171(1), pp. 143-187 (1947).
Shifman, et al., "Heme Redox Potential Control in de Novo Designed Four-a-Helix Bundle Proteins," Biochemistry 39(48), pp. 14813-14821 (2000).
Silva, et al., "Selective Differentiation of Neural Progenitor Cells by High-Epitope Density Nanofibers," Science 303(5662), pp. 1352-1355 (2004).
Solomon, et al., "Engineering the Assembly of Heme Cofactors in Man-Made Proteins," Journal of the American Chemical Society 136(8), pp. 3192-3199 (2014).
Spiro & Wasbotten, "CO as a vibrational probe of heme protein active sites," Journal of Inorganic Biochemistry 99(1), pp. 34-44 (2005).
Sugishima, et al., "Crystal structure of rat heme oxygenase-1 in complex with heme," FEBS Letters 471(1), pp. 61-66 (2000).
Takano & Dickerson, "Redox conformation changes in refined cytochrome c," Proceedings of the national Academy of Sciences USA 77(11), pp. 6371-6375 (1980).
Toft, et al., "Coassembled Cytotoxic and Pegylated Peptide Amphiphiles Form Filamentous Nanostructures with Potent Antitumor Activity in Models of Breast Cancer," ACS Nano 6(9), pp. 7956-7965 (2012).
Trent, et al., "Structural properties of soluble peptide amphiphile micelles," Soft Matter 7, pp. 9572-9582 (2011).
Tysseling-Mattiace, et al., "Self-assembling nanofibers inhibit glial scar formation and promote axon elongation after spinal cord injury," Journal of Neuroscience 28(14), pp. 3814-3823 (2008).
Vojtechovsky, et al., "Crystal structures of myoglobin-ligand complexes at near-atomic resolution," Biophysical Journal 77(4), pp. 2153-2174 (1999).
Walker, "Magnetic spectroscopic (EPR, ESEEM, Mossbauer, MCD and NMR) studies of low-spin ferriheme centers and their corresponding heme proteins," Coordination Chemistry Reviews 185-186, pp. 471-534 (1999).
Webber, M.J., et al., "Controlled Release of Dexamethasone from Peptide Nanofiber Gels to Modulate Inflammatory Response," Biomaterials, Oct. 2012, 33(28), pp. 6823-6832.
Weichsel, et al., "Nitric oxide binding to nitrophorin 4 induces complete distal pocket burial," Nature Structural Biology vol. 7, pp. 551-554 (2000).
Xue, et al, "Carbon monoxide and nitric oxide as coneurotransmitters in the enteric nervous system: Evidence from genomic deletion of biosynthetic enzymes," Proceedings of the National Academy of Sciences USA 97(4), pp. 1851-1855 (2000).
Zhang, et al., "Electron transfer by domain movement in stockbroker bc1," Nature 392, pp. 677-684 (1998).
Zoppellaro, et al, "Studies of Ferric Heme Proteins with Highly Anisotropic/Highly Axial Low Spin (S=½) Electron Paramagnetic Resonance Signals with bis-Histidine and Histidine-Methionine Axial Iron Coordination," Biopolymers 91(12), pp. 1064-1082 (2009).
Zoppellaro, et al., "Low-temperature EPR and Mossbauer spectroscopy of two cytochromes with His-Met axial coordination exhibiting HALS signals," ChemPhysChem 7(6), pp. 1258-1267 (2006).

Mahajan & Bhattacharjya, "β-Hairpin Peptides: Heme Binding, Catalysis, and Structure in Detergent Micelles," Angewandte Chemie 52(25), pp. 6430-6434 (2013).
Marques, "Insights into porphyrin chemistry provided by the microperoxidases, the haempeptides derived from cytochrome c," Dalton Transactions 39, pp. 4371-4385 (2007).
Pordea, "Metal-binding promiscuity in artificial metalloenzyme design," Current Opinion in Chemical Biology 25, pp. 124-132 (2015).
Wu, et al., "Peroxidase activity enhancement of myoglobin by two cooperative distal histidines and a channel to the heme pocket," Journal of Molecular Catalysis B: Enzymatic 134(B), pp. 367-371 (2016).
Adams & Thumser, "Haem-peptide-protein interactions: Part 5. The haem undecapeptide microperoxidase-11 (Fe3 MP-11)/human serum albumin (HSA) reaction in aqueous methanolic solution. A simple system demonstrating the effect of hydrophobicity on ligand release from a ligand-protein complex," Journal of Inorganic Biochemistry 50(1), pp. 1-7 (1993).
Atamn & Boyle, "Amyloid-β peptide binds with heme to form a peroxidase: Relationship to the cytopathologies of Alzheimer's disease," Proceedings of the National Academy of Sciences 103(9), pp. 3381-3386 (2006).
Boffi, et al., "Pentacoordinate Hemin Derivatives in Sodium Dodecyl Sulfate Micelles: Model Systems for the Assignment of the Fifth Ligand in Ferric Heme Proteins," Biophysical Journal 77(2), pp. 1143-1149 (1999).
Clark, et al., "Modulating the copper-sulfur interaction in type 1 blue copper azurin by replacing Cys112 with nonproteinogenic homocysteine," Inorganic Chemistry Frontiers 1(2), pp. 153-158 (2014).
Cordova, et al., "Design of a Functional Membrane Protein by Engineering a Heme-Binding Site in Glycophorin A," Journal of the American Chemical Society 129(3), pp. 512-518 (2007).
Cowley, et al., "Insight into Heme Protein Redox Potential Control and Functional Aspects of Six-Coordinate Ligand-Sensing Heme Proteins from Studies of Synthetic Heme Peptides," Inorganic Chemistry 45(25), pp. 9985-10001 (2006).
Cui, et al., "Self-assembly of peptide amphiphiles: From molecules to nanostructures to biomaterials," Peptide Science 94(1), pp. 1-18 (2010).
Deshmukh, et al., "Water ordering controls the dynamic equilibrium of micelle-fibre formation in self-assembly of peptide amphiphiles," Nature Communications 7, 12367, 11 pages (2016).
D'Souza, et al., "Designed multi-stranded heme binding β-sheet peptides in membrane," Chemical Science 7(4), pp. 2563-2571 (2016).
Gharibi, et al., "Vesicular Mixed Gemini-SDS-Hemin-Imidazole Complex as a Peroxidase-Like Nano Artificial Enzyme," The Journal of Physical Chemistry B 115(16), pp. 4671-4679 (2011).
Hill, et al., "Self-Assembly: From Amphiphiles to Chromophores and Beyond," Molecules 19(6), pp. 8589-8609 (20104).
Hu, et al., "Metalloprotein design using genetic code expansion," Chemical Society Reviews 43(18), pp. 6498-6510 (2014).
Hyster & Ward, "Genetic Optimization of Metalloenzymes: Enhancing Enzymes for Non-Natural Reactions," Angewandte Chemie 55(26), pp. 7344-7357 (2016).
Korendovych & Degrado, "Catalytic efficiency of designed catalytic proteins," Current Opinion in Structural Biology 27, pp. 113-121 (2014).
Kumar & Bandyopadhyay, "Free heme toxicity and its detoxification systems in human," Toxicology Letters 157(3), pp. 175-188 (2005).
Lewis, "Metallopeptide catalysts and artificial metalloenzymes containing unnatural amino acids," Current Opinion in Chemical Biology 25, pp. 27-35 (2015).
Lombardi, et al., "Design of a New Mimochrome with Unique Topology," Chemistry—A European Journal 9(22), pp. 5643-5654 (2003).
Lu, "Design and engineering of metalloproteins containing unnatural amino acids or non-native metal-containing cofactors" Current Opinion in Chemical Biology 9(2), pp. 118-126 (2005).

(56) References Cited

OTHER PUBLICATIONS

Lu, et al., "Design of functional metalloproteins," Nature 460, pp. 855-862 (2009).

Makhlynets, et al., "Short Self-Assembling Peptides Are Able to Bind to Copper and Activate Oxygen," Angewandte Chemie 55(31), pp. 9017-9020 (2016).

Marchi-Delapierre, et al., "Oxidation Catalysis by Rationally Designed Artificial Metalloenzymes," Israel Journal of Chemistry 55(1), pp. 61-75 (2015).

Moffet, et al., "Peroxidase Activity in Heme Proteins Derived from a Designed Combinatorial Library," Journal of the American Chemical Society 122(31), pp. 7612-7613 (2000).

Moosavi-Movahedi, et al., "Micellar histidinate hematin complex as an artificial peroxidase enzyme model: Voltammetric and spectroscopic investigations," Colloids and Surfaces A: Physiochemical and Engineering Aspects 320(1-3), pp. 213-221 (2008).

Nantes, et al., "Modulation of the catalytic activity of porphyrins by lipid-and surfactant-containing nanostructures," Journal of the Brazilian Chemical Society 22(9), pp. 1621-1633 (2011).

Nastri, et al., "Design and engineering of artificial oxygen-activating metalloenzymes," Chemical Society Reviews 45(18), pp. 5020-5054 (2016).

Oohora & Hayashi, "Hemoprotein-based supramolecular assembling systems," Current Opinion in Chemical Biology 19, pp. 154-161 (2014).

Petrik, et al., "Metalloenzyme design and engineering through strategic modifications of native protein scaffolds," Current Opinion in Chemical Biology 19, pp. 67-75 (2014).

Qu, et al., "Hemin-Block Copolymer Micelle as an Artificial Peroxidase and Its Applications in Chromogenic Detection and Biocatalysis," ACS Applied Materials & Interfaces 6(21), pp. 19207-19216 (2014).

Ranieri, et al., "Redox and Electrocatalytic Properties of Mimochrome VI, a Synthetic Heme Peptide on Gold," Langmuir 26(23), pp. 17831-17835 (2010).

Rufo, et al., "Short peptides self-assemble to produce catalytic amyloids," Nature Chemistry 6, pp. 303-309 (2014).

Trent, et al., "Structural properties of soluble peptide amphiphile micelles," Soft Matter 7(20), pp. 9572-9582 (2011).

Vitale, et al., "An artificial heme-enzyme with enhanced catalytic activity: evolution, functional screening and structural characterization," Organic & Biomolecular Chemistry 13(17), pp. 4859-4868 (2015).

Vitale, et al., "Spectroelectrochemistry of FeIII- and CoIII-mimochrome VI artificial enzymes immobilized on mesoporous ITO electrodes," Chemical Communications 50(15), pp. 1894-1896 (214).

Yu, et al., "Protein Design: Toward Functional Metalloenzymes," Chemical Reviews 114(7), pp. 3495-3578 (2014).

* cited by examiner

Heme
Toxic when free in the body

Heme Oxygenase I
Breaks down heme resulting in an anti-inflammatory response

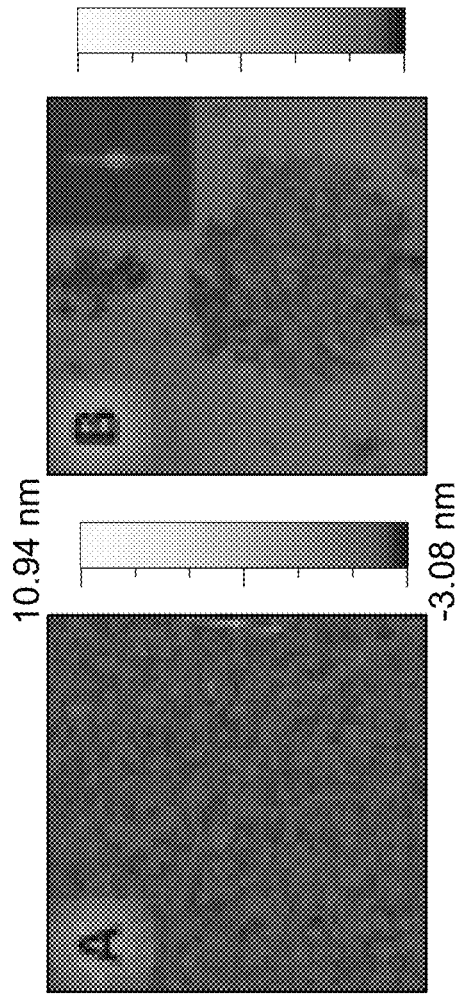
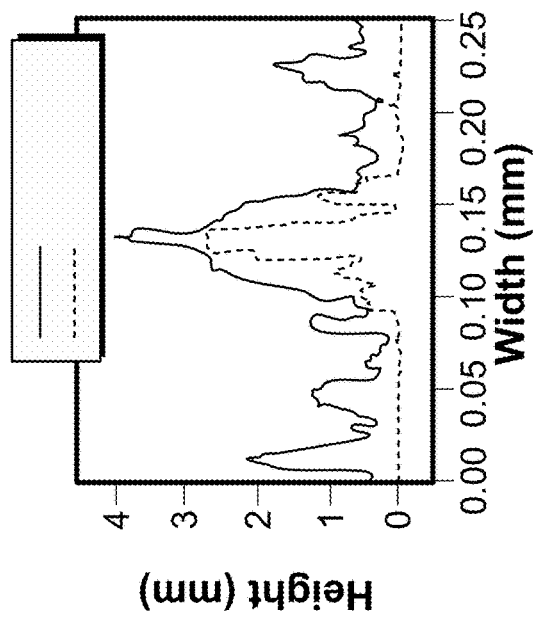
Fig. 7A  Fig. 7B
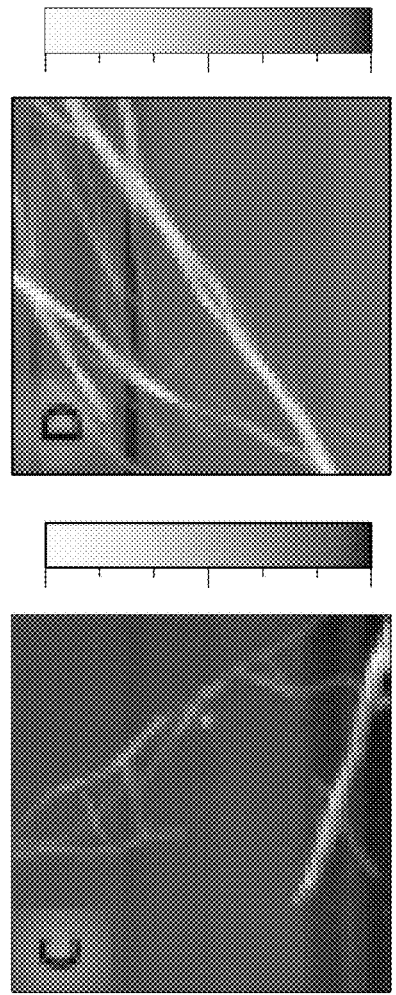
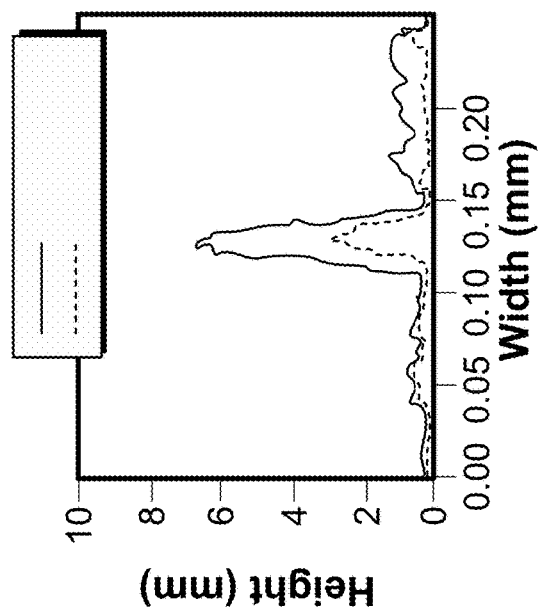
Fig. 7C  Fig. 7D

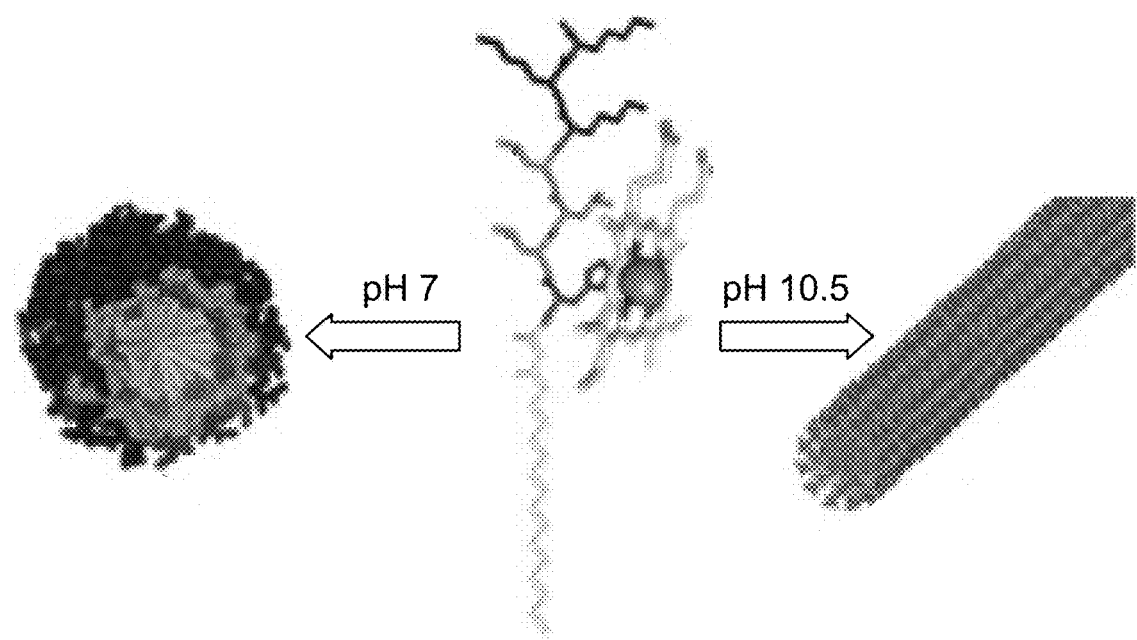
Fig. 7E
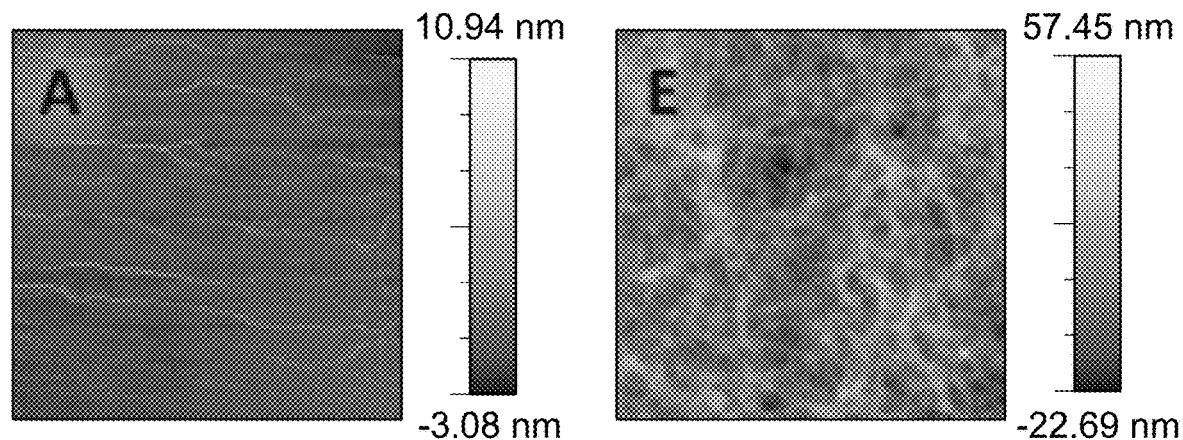
Fig. 8A          Fig. 8E

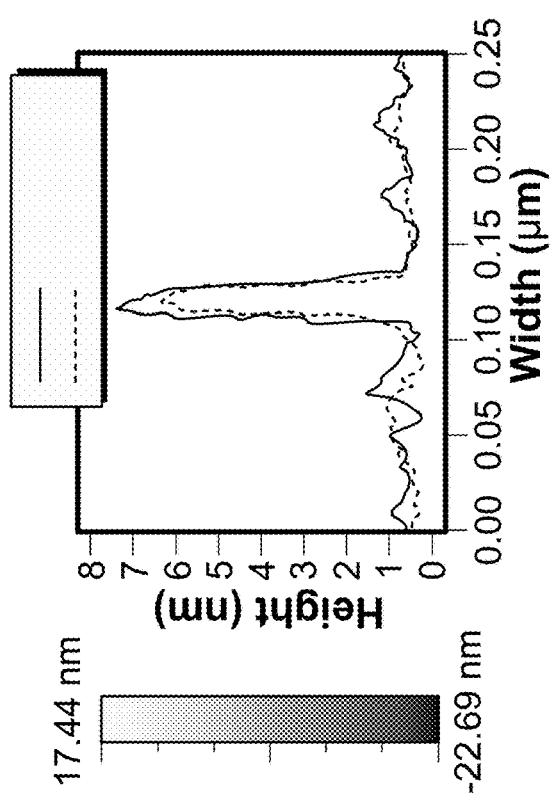
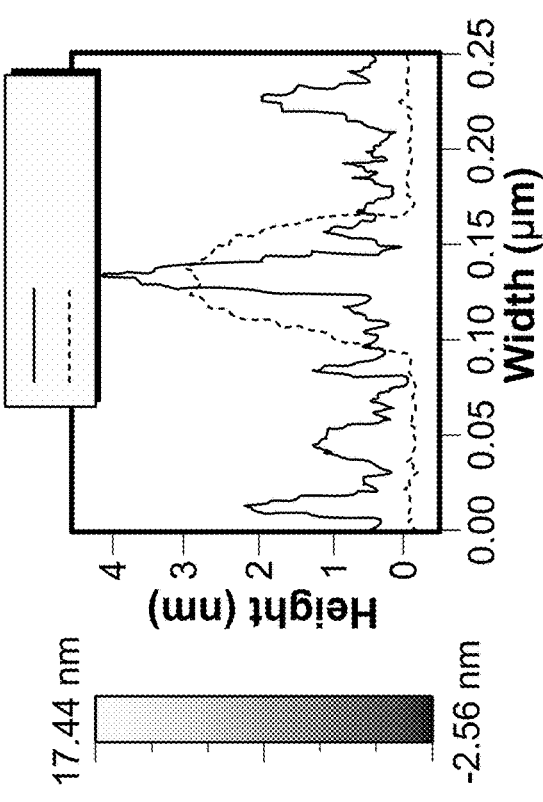
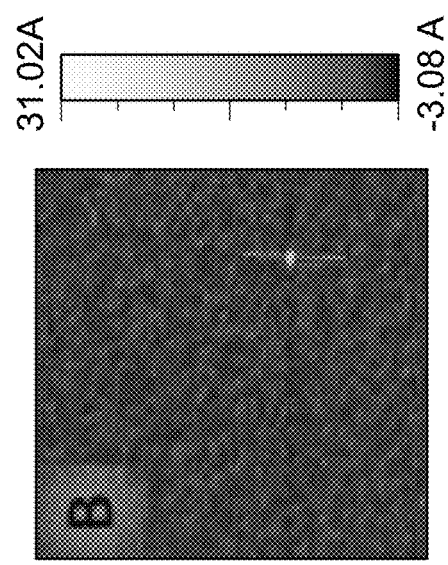
Fig. 8B
Fig. 8F
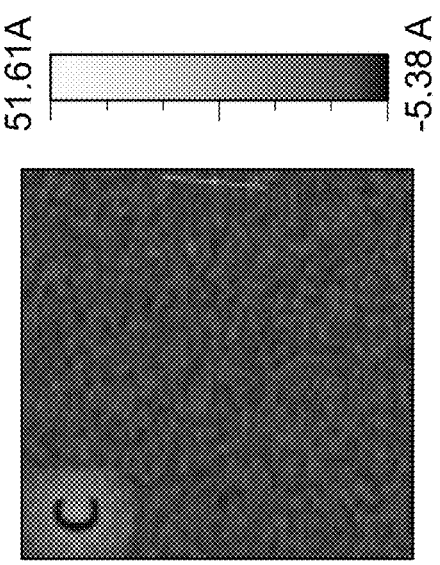
Fig. 8C
Fig. 8G

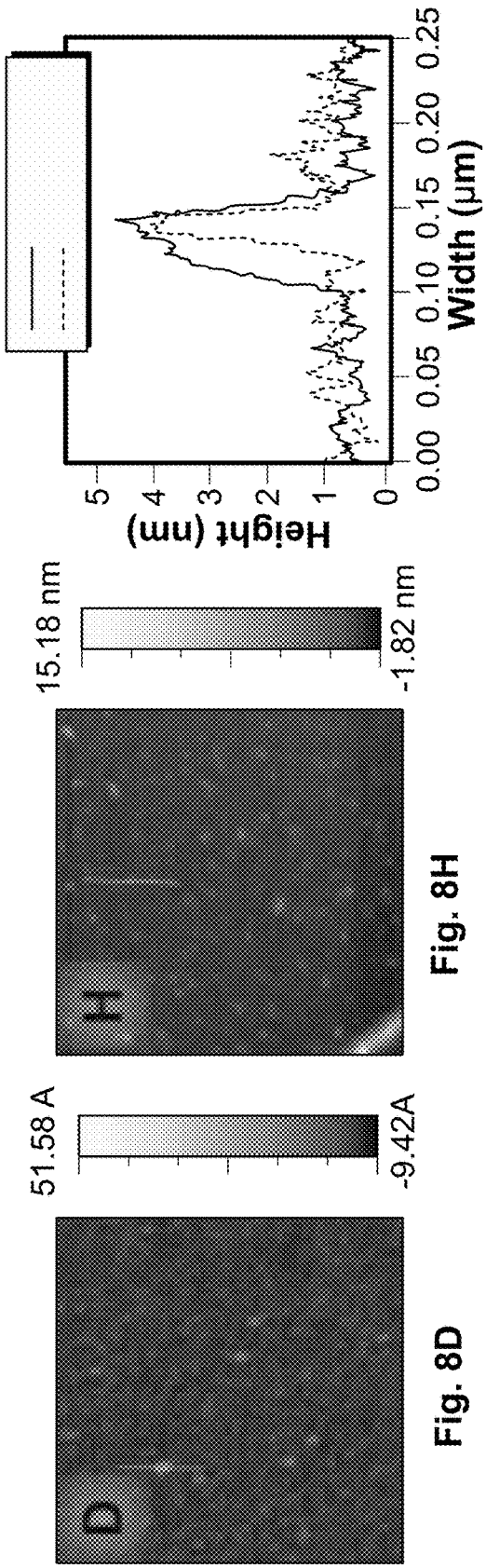
Fig. 8D
Fig. 8H
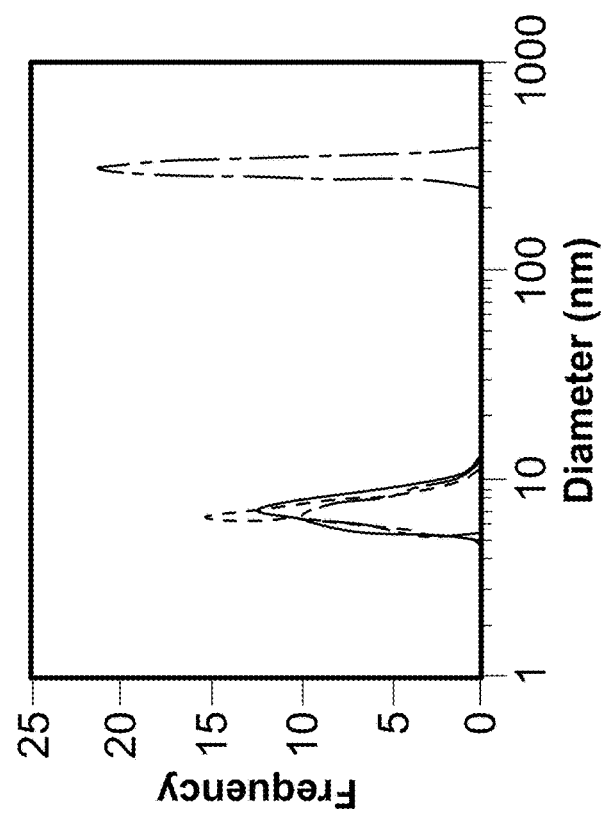
Fig. 9

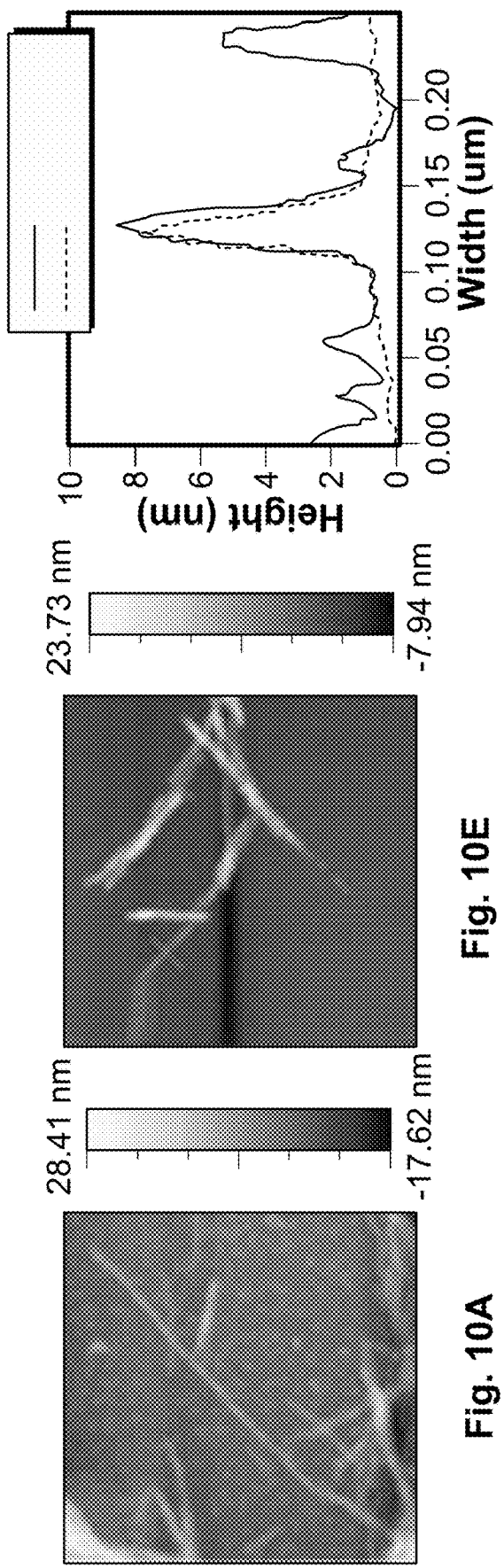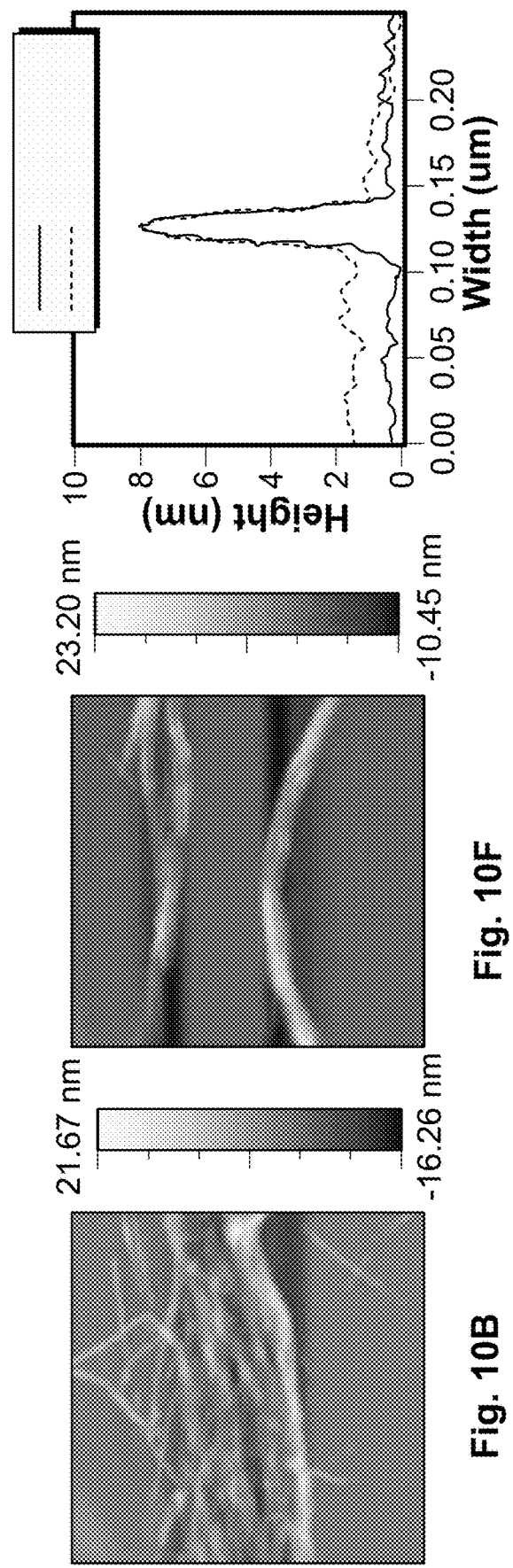
Fig. 10A  Fig. 10E
Fig. 10B  Fig. 10F

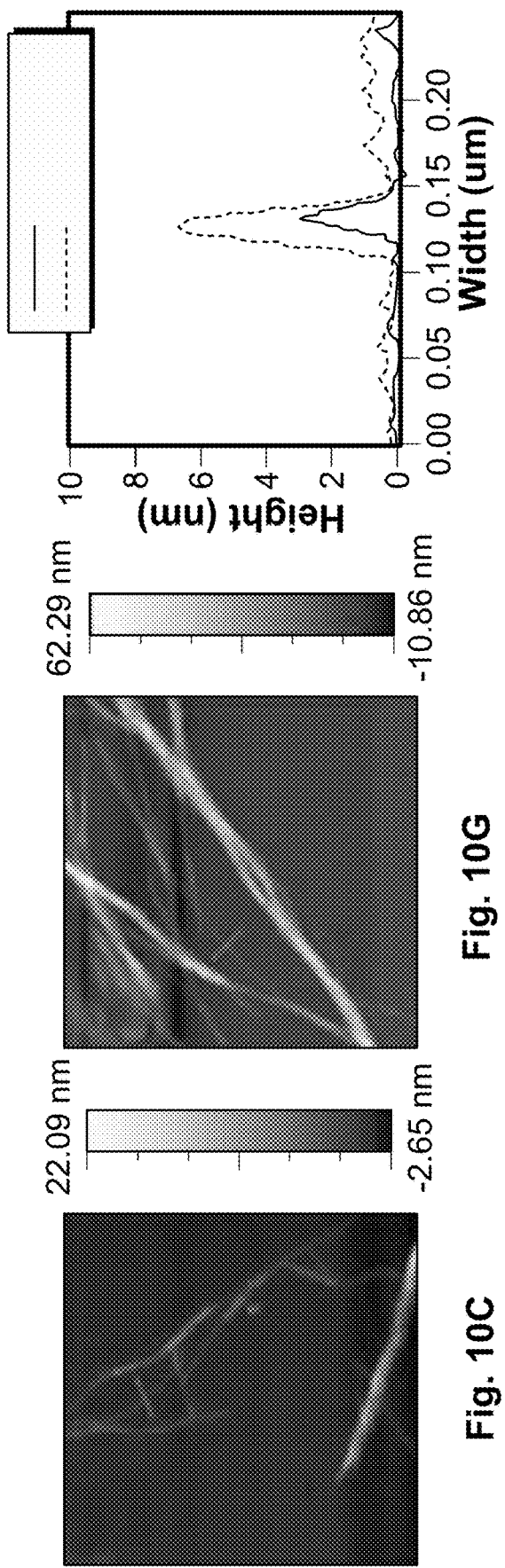
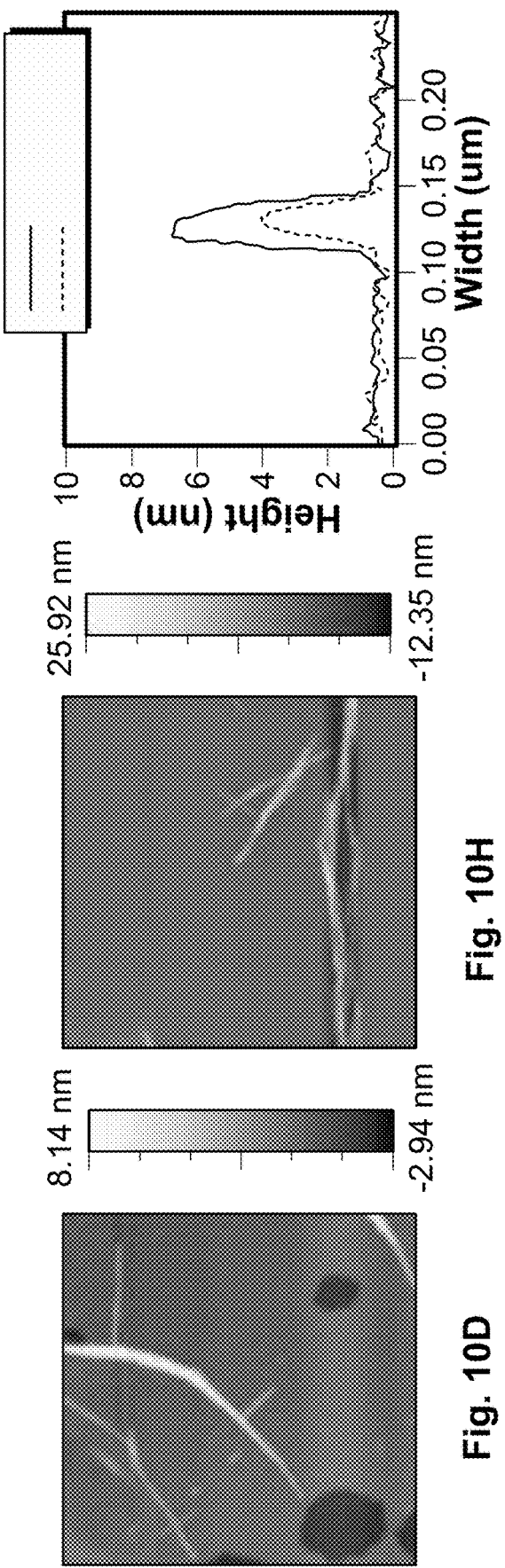
Fig. 10C
Fig. 10G
Fig. 10D
Fig. 10H

| Pepside/Protein | pH | Morphology | $K_d$ | Soret | Q-band | EPR | |
|---|---|---|---|---|---|---|---|
| PAHeme^AA | pH = 7 | Fiber | 360 μM | 401 nm | 567(610 sh) nm | $g_i = 5.96g, g = 2.05$ | H.S. |
| | pH = 10.5 | Fiber | 31 μM | 404 nm | 563, 597 nm | $g_i = 5.96g, g = 2.05$ | H.S. |
| Free Heme | | | | 385 nm | 507, 542 nm | $g_i = 5.96g, g = 2.05$ | H.S. |
| PAHeme^AH | pH = 7 | Micelle | 23 μM | 413 nm | 535, 560, 610 nm | $g_c = 3.03, g_y = 2.32, g_x = 1.57$ | L.S. |
| | pH = 10.5 | Fiber | 3.1 μM | 409 nm | 526, 550 nm | $g_i = 5.96g, g = 2.05$ | H.S. |
| Nitrophorin (AH) | | | | 406 nm | 500 nm (br) | $g_i = 6, g = 2$ | H.S. |
| PAHeme^HH | pH = 7 | Micelle | 2.5 μM | 413 nm | 535, 560 nm | $g_c = 3.03, g_c = 2.32, g_x = 1.57$ | L.S. |
| | pH = 10.5 | Fiber | 5.7 μM | 412 nm | 532, 563 nm | $g_c = 3.03, g_c = 2.32, g_x = $ N.D. | L.S. |
| Neuroglobin (HH) | | | | 412 nm | 534, 557, 610 nm | $g_i = 3.1g_y = 2.1g = 1.3$ | L.S. |
| PAHeme^MH | pH = 7 | Micelle | 66 μM | 410 nm | 535, 560, 610 nm | $g_i = 5.96g, g = 2.05$ | H.S. |
| | pH = 10.5 | Fiber | 148 μM | 406 nm | 568, 599 nm | $g_i = 5.96g, g = 2.05$ | H.S. |
| Cytochrome c (MH) | | | | 405 nm | 530 nm | $g_{xxxx} = 3.3$ | L.S. |

Fig. 13E $$A = Ao + \frac{E_B{}^1}{2} \times \left( \left(\frac{x}{n} \times M + K_D + M\right) - \sqrt{\left(\frac{x}{n} \times M + K_D + M\right)^2 - 4 \times \frac{x}{n} \times M^2} \right)$$

$$-E_S \times I \times M + \frac{E_S{}^1}{2} \times \left( \left(\frac{x}{n} \times M + K_D + M\right) - \sqrt{\left(\frac{x}{n} \times M + K_D + M\right)^2 - 4 \times \frac{x}{n} \times M^2} \right)$$

Gauss

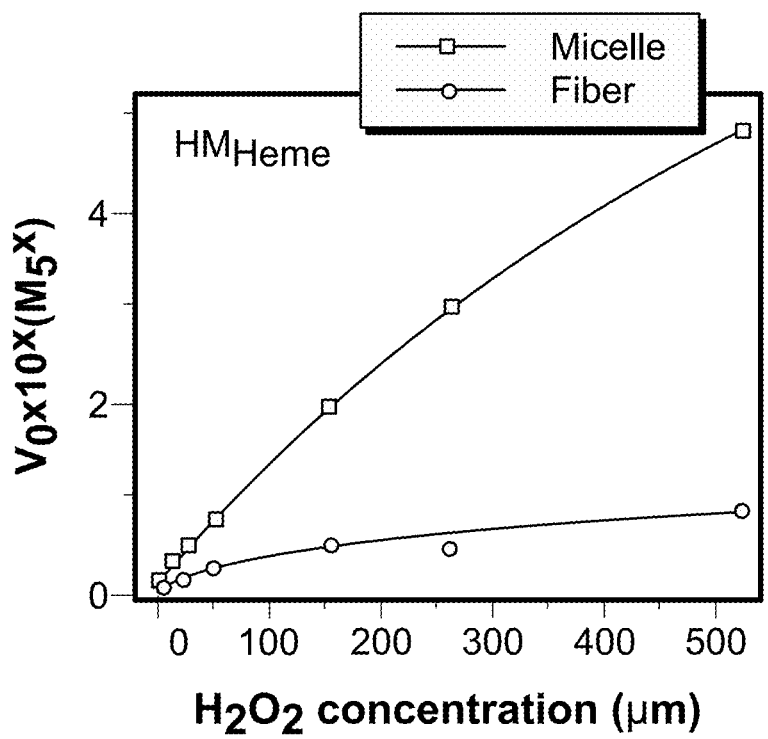

Fig. 19C

| Protein | Morphology | xxxx | xxxx | xxxx |
|---|---|---|---|---|
| $HA_{Heme}$ | Micelle<br>Fiber | xxxxxx<br>xxxxxx | xxxxxx<br>xxxxxx | xxxxxx<br>xxxxxx |
| $HM_{Heme}$ | Micelle<br>Fiber | xxxxxx<br>xxxxxx | xxxxxx<br>xxxxxx | xxxxxx<br>xxxxxx |
| $HH_{Heme}$ | Micelle<br>Fiber | xxxxxx<br>xxxxxx | xxxxxx<br>xxxxxx | xxxxxx<br>xxxxxx |
| $AA_{Heme}$ | Micelle<br>Fiber | xxxxxx<br>xxxxxx | xxxxxx<br>xxxxxx | xxxxxx<br>xxxxxx |

Fig. 19D c16-AAL3K3-CO2H
Chemical Formula: $C_{10}H_{110}N_{10}O_{10}$
Exact Mass: 1253.90 c16-AHL3K3-CO2H
Chemical Formula: $C_{10}H_{110}N_{13}O_{10}$
Exact Mass: 1187.57 c16-HHL₃K₃-CO₂H
Chemical Formula: $C_{10}H_{110}N_{13}O_{10}$
Exact Mass: 1253.90 c16-MHL3K3-CO2H
Chemical Formula: $C_{10}H_{110}N_{13}O_{10}S$
Exact Mass: 1247.55

| Protein | Morphology | TMB Oxidized (μM) |
|---|---|---|
| PA$_{Heme}$-AH | Micelle<br>Fiber | 196.92<br>83.84 |
| PA$_{Heme}$-HH | Micelle<br>Fiber | 226.15<br>150.25 |
| PA$_{Heme}$-MH | Micelle<br>Fiber | 238.20<br>78.46 |
| PA$_{Heme}$-AA | Micelle<br>Fiber | 58.46<br>78.20 |
Fig. 23
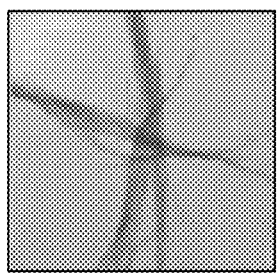 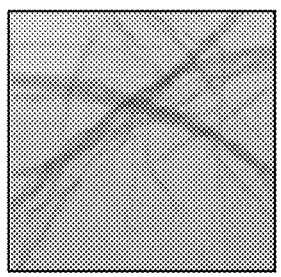 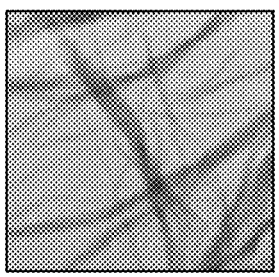 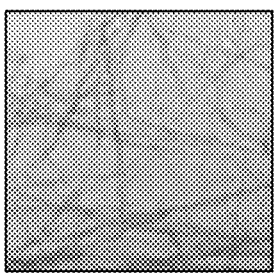
Fig. 24A  Fig. 24B  Fig. 24C  Fig. 24D
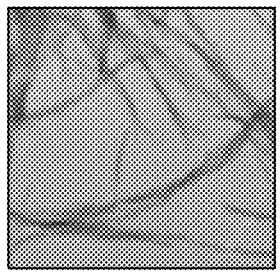 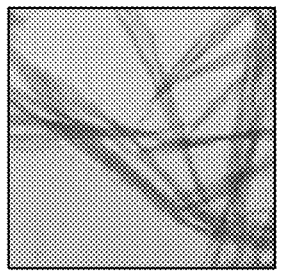 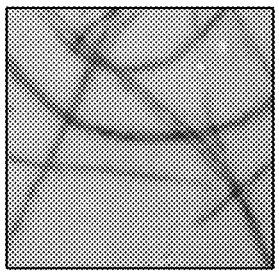 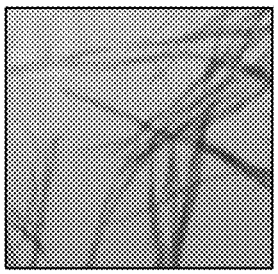
Fig. 24E  Fig. 24F  Fig. 24G  Fig. 24H

SEQUENCE LISTING

```
<160> NUMBER OF SEQ ID NOS: 10

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ile Lys Val Ala Val
1               5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 2

Leu Arg Lys Lys Leu Gly Lys Ala
1               5

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ala His Leu Leu Leu Lys Lys Lys
1               5

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

His His Leu Leu Leu Lys Lys Lys
1               5

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Met His Leu Leu Leu Lys Lys Lys
1               5

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Leu Leu Leu Gly Gly Gly
1               5

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ala His Leu Leu Leu Gly Gly Gly
1               5

<210> SEQ ID NO 8
<211> LENGTH: 8
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ala, His, Met, Thr, Phe, Asn, Asp, Cys or Leu

<400> SEQUENCE: 8

Xaa His Leu Leu Leu Lys Lys Lys
1               5

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ala Ala Leu Leu Leu Lys Lys Lys
1               5

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: May or may not be present

<400> SEQUENCE: 10

Arg Gly Asp Ser
1
```

HEME PEPTIDE MATERIALS FOR ANTI-INFLAMMATORY REGENERATIVE NANOBIOMEDICINE

CROSS-REFERENCE TO RELATED APPLICATION

This application claims the benefit of and priority to U.S. Provisional Application No. 62/431,119, filed on Dec. 7, 2016, the content of which is incorporated herein by reference in its entirety.

STATEMENT OF GOVERNMENT SUPPORT

The United States Government claims certain rights in this invention pursuant to Contract No. W-31-109-ENG-38 between the United States Government and the University of Chicago and/or pursuant to DE-AC02-06CH11357 between the United States Government and UChicago Argonne, LLC representing Argonne National Laboratory.

SEQUENCE LISTING

The instant application contains a Sequence Listing which has been submitted electronically in ASCII format and is hereby incorporated by reference in its entirety. Said ASCII copy, created on Mar. 15, 2018, is named 051583-0819_SL.txt and is 2,579 bytes in size.

BACKGROUND

Controlling catalytic activity through the non-covalent organization and assembly of molecules in a precise arrangement is at the heart of many biological processes and remains a challenge in supra-molecular nano-architectures. Proteins, simply stated, achieve this through a chain of amino acids that fold into a three-dimensional structure that in turn governs the molecules activity. Achieving complex biologically inspired reactivity in synthetic materials remains a challenge because of the need to simultaneously balance properties that lead to supramolecular assembly while maintaining precise molecular control near the catalytic active site. Peptide-amphiphiles, a class of supramolecular bio-based materials typically employed in regenerative medicine, provide an impressively simple solution to this problem. (1-3) The peptide serves as a scaffold with recognition, structural, and functional sites. The structural region guides assembly while the functional site, typically a modified or unnatural amino acid or sequence of amino acids, is used in mineralization or catalysis. (4-9) The peptide component, however, is highly underutilized and can be further programmed to incorporate function, ultimately generating a protein-like catalytic material. (10,11) However, peptide-amphiphile like many implanted biomaterials run into the problem of producing an inflammatory response due to damaged tissue produced from material implementation and often hinder the efficacy of the material.

SUMMARY OF THE INVENTION

Aspects of this disclosure relate to a peptide amphiphile according to the formula:

$$c\#-xHy_3z_3$$

wherein: x=Ala, His, Met, Thr, Phe, Asn, Asp, Cys, Leu y=Ala, Val, Leu, Ile, Phe, Trp z=Lys, Glu, Gly c#=a linear carbon chain 8 to 16 units in length at the N-terminus.

A non-limiting exemplary embodiment of this peptide amphiphile is the peptide amphiphile provided by the formula:

$$c16-xHy_3z_3$$

wherein:
x=Ala, His, Met, Thr, Phe, Asn, Asp, Cys, Leu
y=Ala, Val, Leu, Ile, Phe, Trp
z=Lys, Glu, Gly
c16=palmitoyl moiety at the N-terminus
operatively linked to a biorecognition site or epitope.

In some embodiments, the peptide amphiphile is operatively linked to a heparin binding domain in an effort to target diseases where fast wound healing is required while simultaneously promoting an anti-inflammatory response. In further embodiments, the biorecognition site or epitope is selected from the group consisting of but not limited to (i) RGD(S) (SEQ ID NO: 10) which serves as a cell adhesion/integrin targeting epitope, (ii) IKVAV (SEQ ID NO: 1) that mimics laminin of the extracellular matrix to promote cell attachment and growth, and (iii) LRKKLGKA (SEQ ID NO: 2) that binds heparin sulfate that is integral in promoting angiogenesis and furthermore wound healing.

In a certain embodiment, x is Ala, y is Leu, and z is Glu. In some embodiments, the peptide amphiphile has a formula selected from the group consisting of c16-AHL$_3$K$_3$—CO$_2$H (SEQ ID NO: 3), c16-HHL$_3$K$_3$—CO$_2$H (SEQ ID NO: 4), and c16-MHL$_3$K$_3$—CO$_2$H (SEQ ID NO: 5).

Additional aspects of the disclosure relate to a composition comprising a plurality of the peptide amphiphile and a pharmaceutically acceptable carrier. In some embodiments, the pharmaceutically acceptable carrier is sterile water.

Further aspects of the disclosure relate to a method of treating a disease, disorder, or condition associate with an anti-inflammatory mechanism comprising administering the composition or peptide. In some embodiments, the disease, disorder, or condition is cardiovascular disease, optionally a cardiovascular disease known to lead to myocardial infarction.

BRIEF DESCRIPTION OF THE DRAWINGS

FIGS. 3A-3E depict a schematic diagrams of the anti-inflammatory peptide-amphiphiles disclosed herein.

FIGS. 7A-7E provides characterization of supramolecular morphologies in different aqueous solutions. atomic force micrographs (2 μm×2 μm) of HH assemblies in HEPES 7A without and 7B with hemin and in 10 mM $NH_4OH$ HEPES 7C without and 7D with hemin. The height profiles to the right of the micrographs are measurements of individual micelles or fibers with-out, black; and with hemin, red. 7E is a graphical representation of the spherical micelles at pH 7 and the long-aspect ratio nanofibers at pH 10.5.

FIGS. 8A-8H show atomic force micrographs (2 μm×2 μm) of peptide amphiphile assemblies in HEPES without hemin: A. $PA_{Heme}$-AA, B. $PA_{Heme}$-AH, C. $PA_{Heme}$-HH, D. $PA_{Heme}$-MH, and with hemin E. $PA_{Heme}$-AA, F. $PA_{Heme}$-AH, G. $PA_{Heme}$-HH, H. $PA_{Heme}$-MH. The height profiles to the right of the micrographs are measurements of individual fibers without hemin, black; and with hemin, red.

FIG. 9 is a graph of dynamic light scattering of $PA_{Heme}$-AA (blue), $PA_{Heme}$-AH (red), $PA_{Heme}$-HH (green), and $PA_{Heme}$-MH (purple) in HEPES, pH 7.5. All samples were filtered through a 2 μm PTFE syringe filter (EMD Millipore).

FIGS. 10A-10H show atomic force micrographs (2 μm×2 μm) of peptide amphiphile fibrils in 10 mM $NH_4OH$ without hemin: A. $PA_{Heme}$-AA, B. $PA_{Heme}$-AH, C. $PA_{Heme}$-HH, D. $PA_{Heme}$-MH, and with hemin E. $PA_{Heme}$-AA, F. $PA_{Heme}$-AH, G. $PA_{Heme}$-HH, H. $PA_{Heme}$-MH. The height profiles to the right of the micrographs are measurements of individual fibers without hemin, black; and with hemin, red.

FIGS. 13A-13E provide a characterization of ferric heme coordination to different supramolecular constructs; electronic absorption spectroscopy of heme binding in (A) micelles and (B) fibers. EPR spectroscopy in (C) micelles and (D) fibers. Vertical lines and labels mark the high spin (dashed lines) and low spin (solid lines) states. $AA_{Heme}$, Blue; $AH_{Heme}$, Red; $HH_{Heme}$, Green; MHHeme, Purple. FIG. 13E is a table listing characteristics of the peptide-amphiphiles.

FIGS. 19A-19D show the results of testing of peroxidase activities at pH 7 exhibiting dependence on sequence and supramolecular morphology. Peroxidase activity, as seen by the oxidation of TMB, mediated by peptide-amphiphile series in either a (A) micelle or (B) fiber morphology. The activity is significantly diminished depending on the gross structure and heme-coordination environment. Peptide-amphiphile concentration: 10 uM, heme concentration: 1 μM, $H_2O_2$ and TMB concentration: 300 μM, HEPES buffer pH 7. (C) Representative Michaelis-Menten curve for the $HA_{Heme}$ peptide-amphiphile; the other peptide-amphiphiles are in FIG. 20. Peptide-amphiphile concentration: 10 uM, heme concentration: 1 μM, TMB concentration: 300 μM, HEPES buffer pH 7. (D) Rate information for the series of peptide-amphiphiles in this work.

FIG. 23 is a table depicting quantifying the total amount of TMB oxidized over 50 minutes for each peptide in both supramolecular structural states.

FIGS. 24A-24H depict transmission scanning electron micrographs of peptide amphiphile fibrils without hemin: A. $PA_{Heme}$-AA, B. $PA_{Heme}$-AH, C. $PA_{Heme}$-HH, D. $PA_{Heme}$-MH, and with hemin E. $PA_{Heme}$-AA, F. $PA_{Heme}$-AH, G. $PA_{Heme}$-HH, H. $PA_{Heme}$-MH. The scale bar in panel A represents 500 nm.

DETAILED DESCRIPTION

Heme-B (Fe-protoporphyrin IX) has an impressively diverse functional library in nature. Unco-ordinated, it is toxic due to its ability to produce reactive oxygen species. (12) However, when associated with a protein, function can be focused toward important metabolic activities. This is due to the cofactor's immediate coordination environment, which is significantly influenced by the protein structure. (13,14) For example, nitrophorin coordinates heme with a single histidine and, due to its structure, functions as a nitric oxide carrying protein found in insects, FIG. 6. (15-17) Neuroglobin is believed to assist in storing oxygen in the brain and binds the same cofactor with two amino acids (bis-histidine coordination). (18) Cytochrome c uses one histidine and one methionine ligand. It is an electron transfer protein with a high redox potential compared to most heme proteins. (19-23) No artificial material is able to associate with a single cofactor and carry out such different functions, but achieving this level of control would add new dimensions to material applications.

Neuroglobin, cytochrome c, and hemoglobin further control heme-function through large-scale conformational changes. (24-26) Using protein design, Korendovych et al. redesigned a natural protein with existing conformational changes to engineer a novel active site. (27) Similarly, Grosset et al. engineered allosteric rearrangements in a de novo protein, using heme as a redox-switch, but were unable to couple that to a function. (28) The triggers and effects of long-range interactions are well understood in natural systems but translating them to materials and other technologies has been difficult.

Aspects of this disclosure relate to a peptide-based self-assembling material that functions like a natural protein. Further aspects describe the incorporation of the naturally occurring cofactor heme-B to elevate peptide-amphiphiles to a new level of sophistication. Still further aspects relate to a system where the supramolecular structure controls heme-coordination and reactivity.

Figure 1:
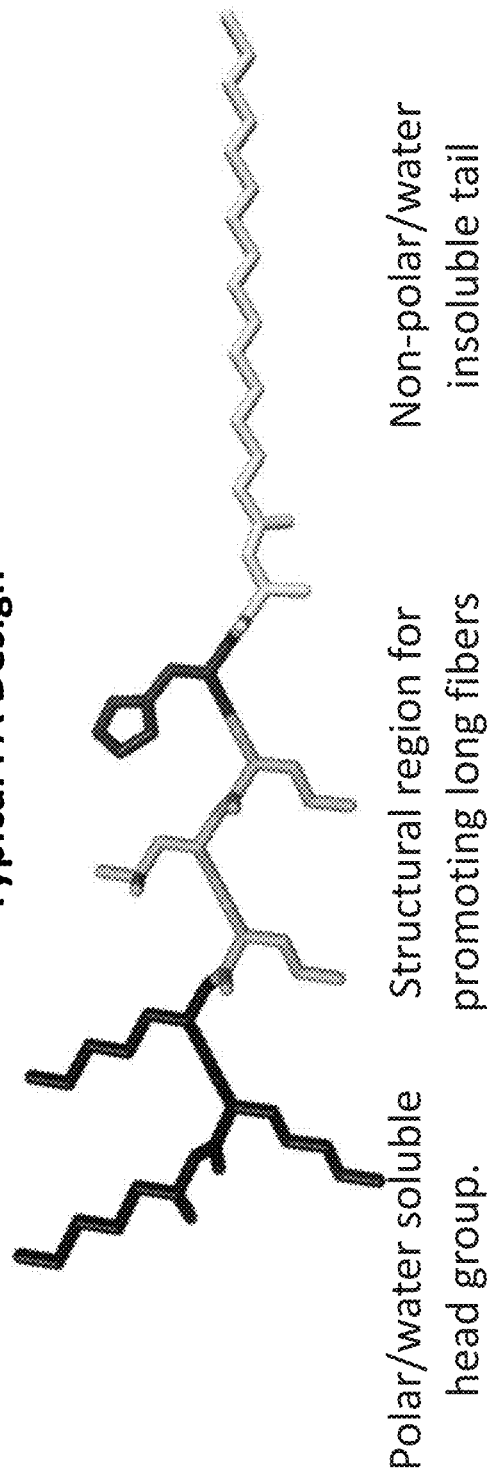
FIG. 1 is a schematic of a conventional peptide-amphiphile.
Figure 2A:
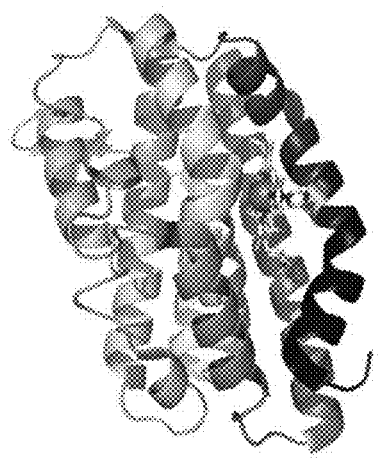
FIG. 2A depicts the structure of free heme, which is toxic when free in the body.
Figure 2B:
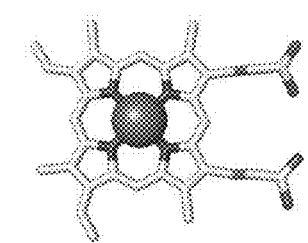
FIG. 2B depicts 3-dimensional structure of heme oxygenase I, which degrades heme (as shown in FIG. 2C) and through this degradation process elicits an anti-inflammatory response.
Figure 2C:
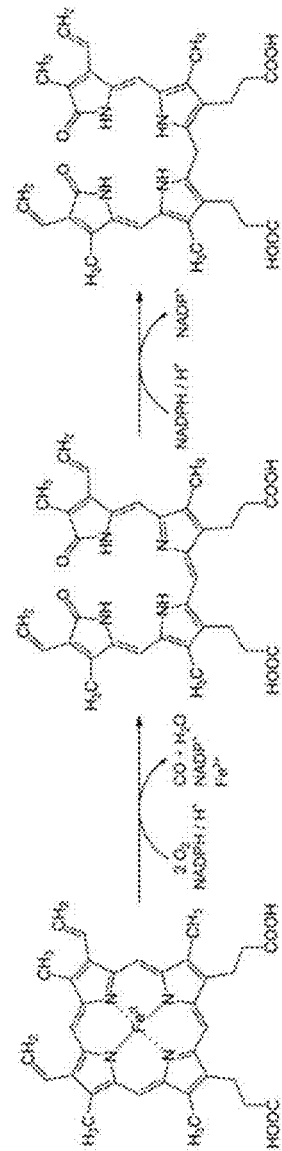
Figure 3E:
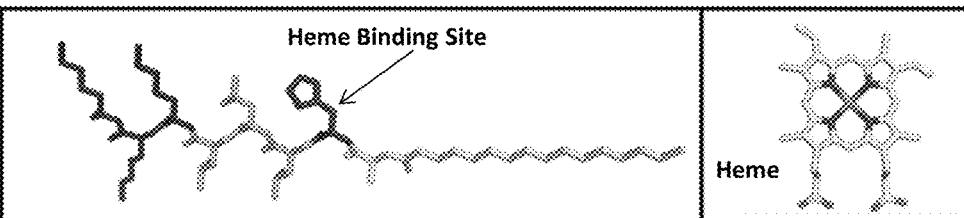
Figure 3E:
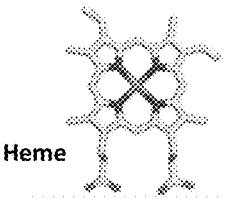
Figure 3E:
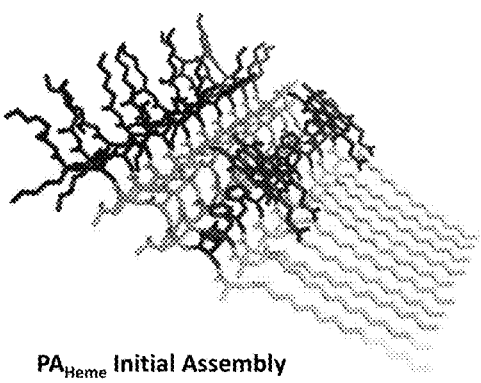
Figure 3E:
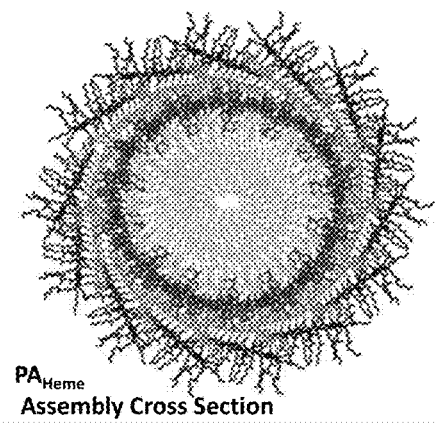
Figure 3E:
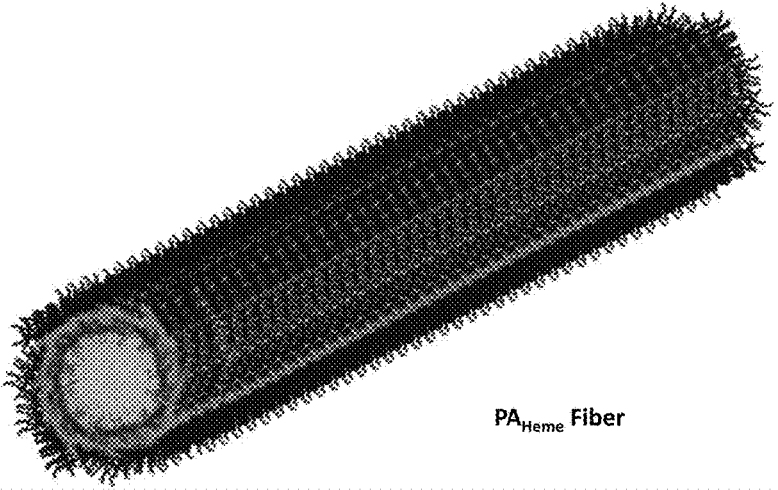
Figure 4:
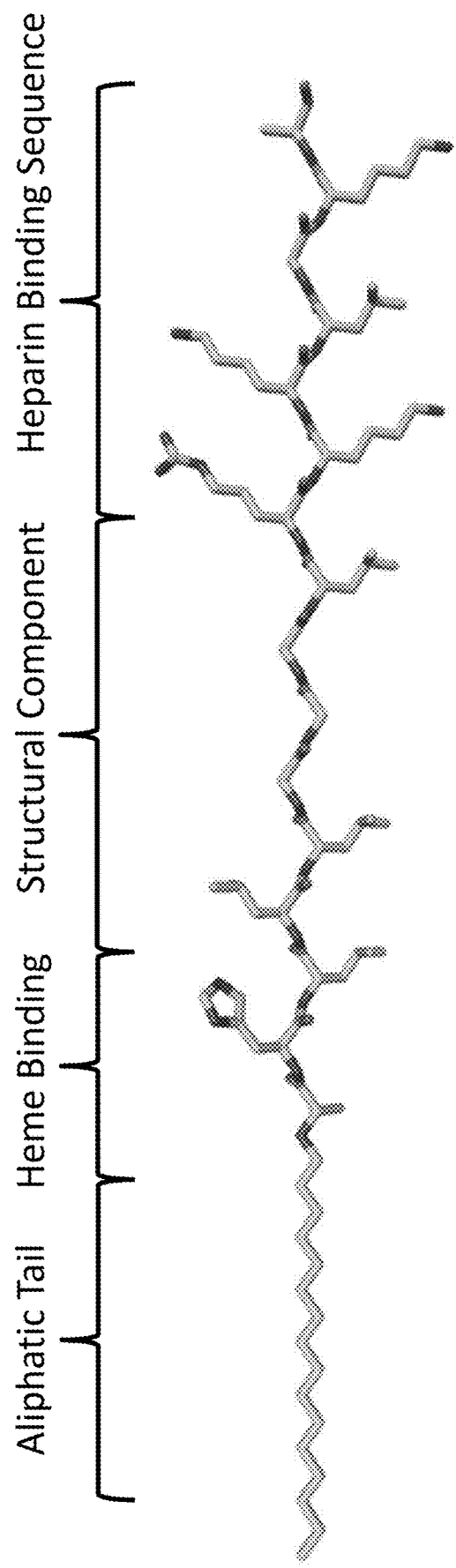
FIG. 4 is a schematic of an exemplary anti-inflammatory peptide-amphiphile comprising an aliphatic tail (palmitoyl), heme binding domain (AH), structural component (LLLGGG (SEQ ID NO: 6), chosen for its beta-sheet propensity), and heparin binding sequence (LRKKLGKA (SEQ ID NO: 2)).
Figure 5:
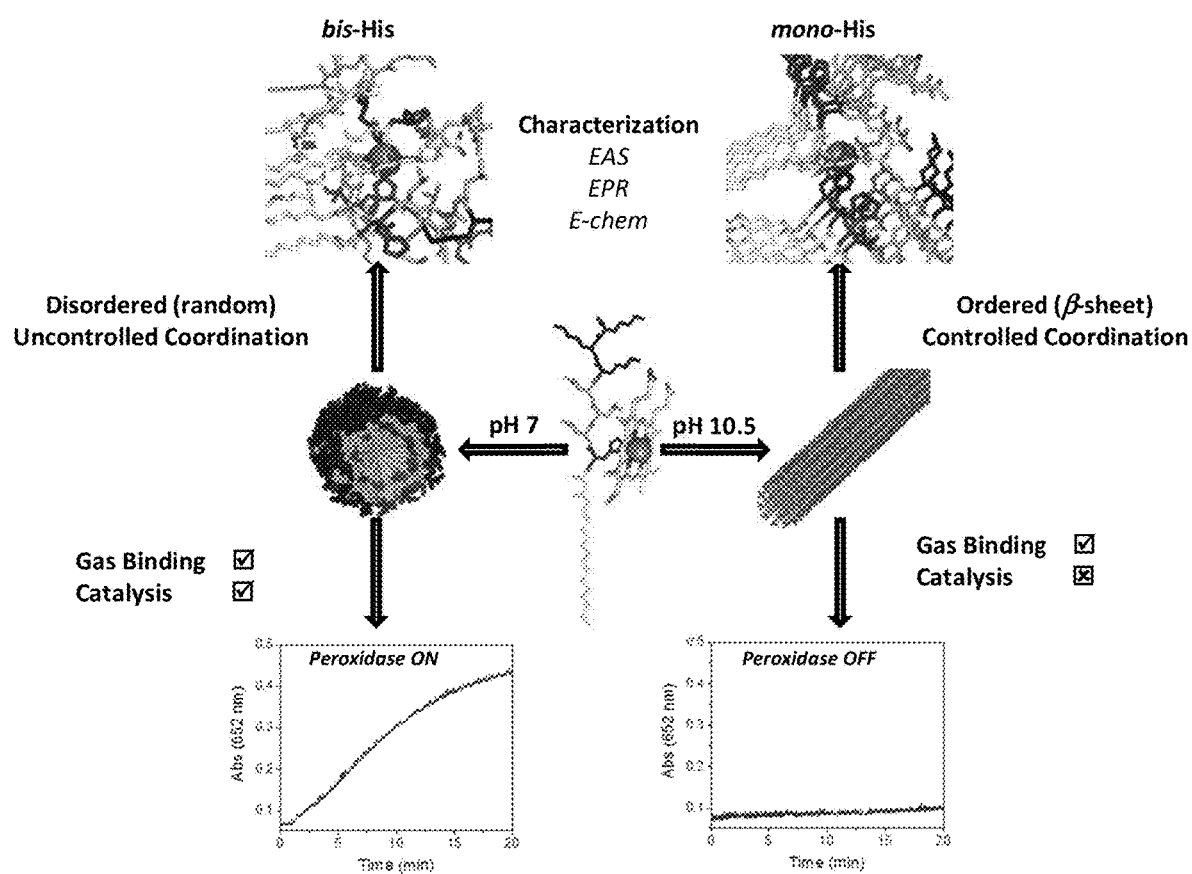
FIG. 5 is a schematic illustrating the impact morphology has (micelles formed at neutral pH and fibers formed at pH >10) on both the coordination mode of the heme molecule and the enzymatic (peroxidase) activity. Peroxidase studies were performed at neutral pH for both the micelles and fibers. Changing the pH from 10.5 to 7.0 does not result in loss of fiber formation.
Figure 6:
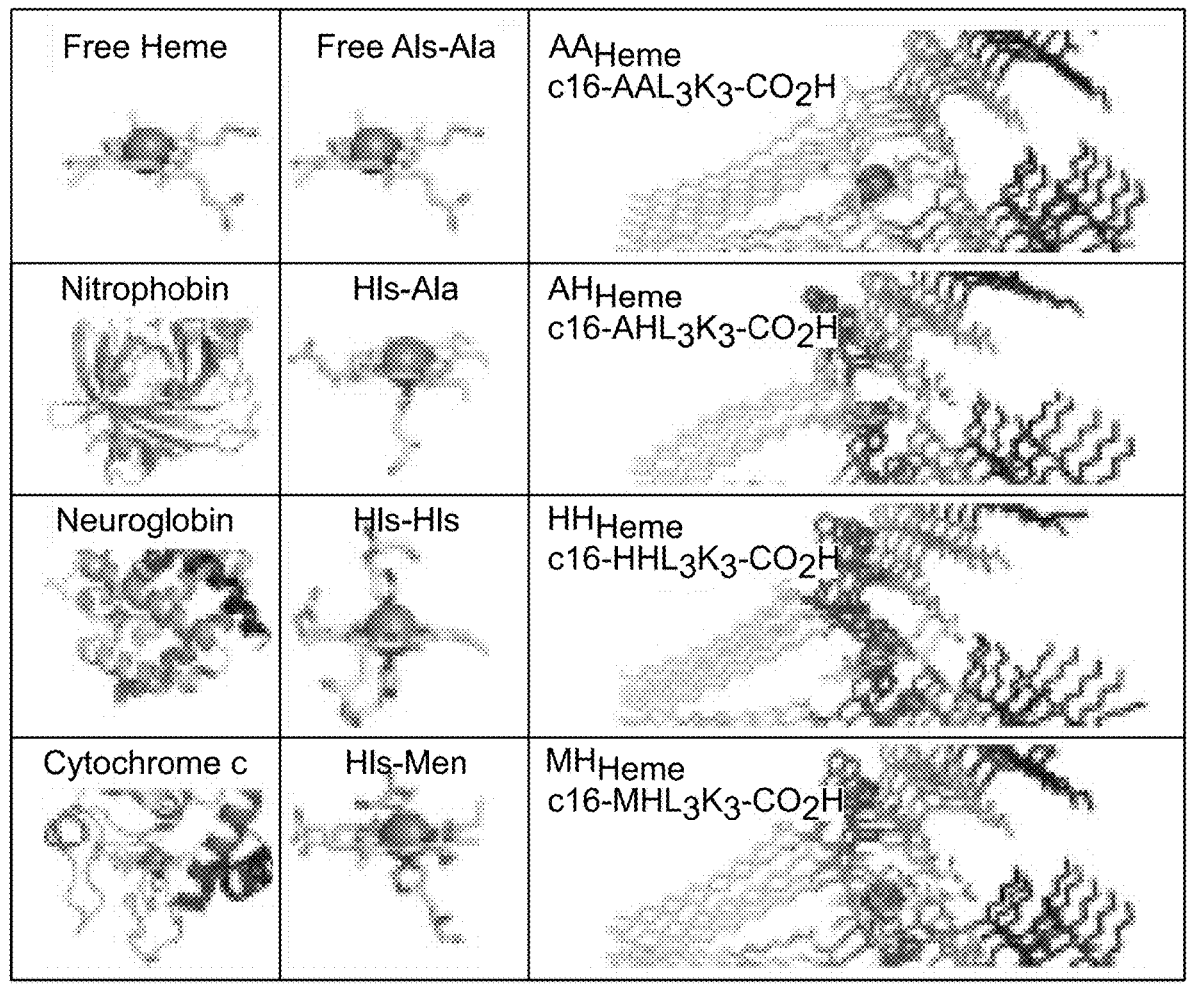
FIG. 6 depicts protein structure, active site and design inspiration for functional heme peptide amphiphiles; cartoon depictions of crystal structures for nitrophorin (PDB ID—1ERX), neuroglobin (PDB ID—2VRY), and Cytochrome c (PDB ID—3CYT); details of the primary coordination sphere highlighting no-coordination, single histidine, bis-histidine, and histidine-methionine; designed heme-binding peptide amphiphiles with their abbreviated names and sequence (SEQ ID NOS: 9 and 3-5, respectively, in order of appearance). Color coding for PAHeme molecules: grey, palmitoyl/c16; yellow, alanine; orange, methionine; red, histidine; green, leucine; blue, lysine.

Applicants demonstrate long-range conformational changes in peptide-amphiphile assemblies and use thereof to control redox properties and reactivity of our non-covalently bound cofactor. Described herein is a peptide-amphiphile with a variant heme-binding site achieved through a single "mutation" within the primary sequence—in turn changing the coordination mode surrounding the heme (FIG. 6). Also described herein is evidence that the resulting supramolecular assembly, micelles versus fibers, significantly influences the heme coordination mode. Further described herein is the disclosed peptide-amphiphile's ability to bind carbon monoxide, which serves as a redox inactive surrogate to other biologically relevant gases like $O_2$ and NO and thus confirms heme active site accessibility for catalysis. Further described herein is the ability to turn on or off heme-based catalysis based on the peptide-amphiphile supramolecular structure micelles versus fibers. These discoveries emphasize the robustness of the peptide-amphiphile in developing next generation, functional, biomolecular materials.

Unless defined otherwise, all technical and scientific terms used herein have the same meanings as commonly understood by one of ordinary skill in the art to which this disclosure belongs. All nucleotide sequences provided herein are presented in the 5' to 3' direction. Although any methods and materials similar or equivalent to those described herein can be used in the practice or testing of the present disclosure, particular, non-limiting exemplary methods, devices, and materials are now described. All technical and patent publications cited herein are incorporated herein by reference in their entirety. Nothing herein is to be construed as an admission that the disclosure is not entitled to antedate such disclosure by virtue of prior invention.

The practice of the present disclosure will employ, unless otherwise indicated, conventional techniques of tissue culture, immunology, molecular biology, microbiology, cell biology and recombinant DNA, which are within the skill of the art. See, e.g., Green and Sambrook eds. (2012) Molecular Cloning: A Laboratory Manual, 4th edition; the series Ausubel et al. eds. (2015) Current Protocols in Molecular Biology; the series Methods in Enzymology (Academic Press, Inc., N.Y.); MacPherson et al. (2015) PCR 1: A Practical Approach (IRL Press at Oxford University Press); MacPherson et al. (1995) PCR 2: A Practical Approach; McPherson et al. (2006) PCR: The Basics (Garland Science); Harlow and Lane eds. (1999) Antibodies, A Laboratory Manual; Greenfield ed. (2014) Antibodies, A Laboratory Manual; Freshney (2010) Culture of Animal Cells: A Manual of Basic Technique, 6th edition; Gait ed. (1984) Oligonucleotide Synthesis; U.S. Pat. No. 4,683,195; Hames and Higgins eds. (1984) Nucleic Acid Hybridization; Anderson (1999) Nucleic Acid Hybridization; Herdewijn ed. (2005) Oligonucleotide Synthesis: Methods and Applications; Hames and Higgins eds. (1984) Transcription and Translation; Buzdin and Lukyanov ed. (2007) Nucleic Acids Hybridization: Modern Applications; Immobilized Cells and Enzymes (IRL Press (1986)); Grandi ed. (2007) In Vitro Transcription and Translation Protocols, 2nd edition; Guisan ed. (2006) Immobilization of Enzymes and Cells; Perbal (1988) A Practical Guide to Molecular Cloning, 2nd edition; Miller and Calos eds, (1987) Gene Transfer Vectors for Mammalian Cells (Cold Spring Harbor Laboratory); Makrides ed. (2003) Gene Transfer and Expression in Mammalian Cells; Mayer and Walker eds. (1987) Immunochemical Methods in Cell and Molecular Biology (Academic Press, London); Lundblad and Macdonald eds. (2010) Handbook of Biochemistry and Molecular Biology, 4th edition; and Herzenberg et al. eds (1996) Weir's Handbook of Experimental Immunology, 5th edition.

All numerical designations, e.g., pH, temperature, time, concentration, and molecular weight, including ranges, are approximations which are varied (+) or (−) by increments of 1.0 or 0.1, as appropriate or alternatively by a variation of +/−15%, or alternatively 10% or alternatively 5% or alternatively 2%. It is to be understood, although not always explicitly stated, that all numerical designations are preceded by the term "about". It also is to be understood, although not always explicitly stated, that the reagents described herein are merely exemplary and that equivalents of such are known in the art.

Definitions

As used in the specification and claims, the singular form "a", "an" and "the" include plural references unless the context clearly dictates otherwise. For example, the term "a polypeptide" includes a plurality of polypeptides, including mixtures thereof.

As used herein, the term "comprising" is intended to mean that the compositions and methods include the recited elements, but do not exclude others. "Consisting essentially of" when used to define compositions and methods, shall mean excluding other elements of any essential significance to the combination for the intended use. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions disclosed herein.

Embodiments defined by each of these transition terms are within the scope of this disclosure.

The term "amphiphile" as used herein refers to a compound which possesses both hydrophilic and hydrophobic properties, for example in separate domains of the compound. When used to modify the term "peptide," the term "amphiphile" may also imply the ability for the peptide-based molecule to self-assemble into supermolecular structures due to the interaction between the hydrophilic and hydrophobic domains.

The term "protein", "peptide" and "polypeptide" are used interchangeably and in their broadest sense to refer to a compound of two or more subunit amino acids, amino acid analogs or peptidomimetics. The subunits may be linked by peptide bonds. In another embodiment, the subunit may be linked by other bonds, e.g., ester, ether, etc. The term "enzyme" as used herein refers to a specific type of protein that serves as a catalyst for a particular reaction.

A protein or peptide must contain at least two amino acids and no limitation is placed on the maximum number of amino acids which may comprise a protein's or peptide's sequence. As used herein the term "amino acid" refers to either natural and/or unnatural or synthetic amino acids, including glycine and both the D and L optical isomers, amino acid analogs and peptidomimetics. The amino acids may be numbered based on a reference sequence to designate their position in the protein or peptide.

As used herein the term "amino acid" refers to either natural and/or unnatural or synthetic amino acids, including, but not limited to, the twenty commonly occurring amino acids alanine (Ala or A), arginine (Arg or R), asparagine (Asn or N), aspartic acid (Asp or D), cysteine (Cys or C), glutamine (Gln or Q), glutamic acid (Glu or E), glycine (Gly or G), histidine (His or H), isoleucine (Ile or I), leucine (Leu or L), lysine (Lys or K), methionine (Met or M), phenylalanine (Phe or F), proline (Pro or P), serine (Ser or S), threonine (Thr or T), tryptophan (Trp or W), tyrosine (Tyr or Y), and valine (Val or V) and both the D or L optical isomers thereof, and amino acid analogs and peptidomimetics. The term "amino acid" is used herein in the conventional sense to refer to organic chemical moieties which comprise an amino group ($-NH_2$) and a carboxylic acid group ($-COOH$). Amino acids may be further grouped based on their side chains, e.g. "hydrophobic amino acids" are those with hydrophobic side chains, including, but not limited to, alanine (A), isoleucine (I), leucine (L), valine (V), phenylalanine (F), tryptophan (W) or tyrosine (Y) and "hydrophilic amino acids" are those with charged or polar side chains, including, but not limited to, arginine (R), asparagine (N), aspartic acid (D), glutamine (Q), glutamic acid (E), histidine (H), lysine (K), serine (S), and threonine (T).

It is to be inferred without explicit recitation and unless otherwise intended, that when the present disclosure relates to a peptide or protein, an equivalent or a biologically equivalent of such is intended within the scope of this disclosure. As used herein, the term "biological equivalent thereof" is intended to be synonymous with "equivalent thereof" when referring to a reference protein or peptide, intends those having minimal homology while still maintaining desired structure or functionality. Unless specifically recited herein, it is contemplated that any peptide or protein mentioned herein also includes equivalents thereof. In one aspect, an equivalent intends at least about 80% homology or identity and alternatively, at least about 85%, or alternatively at least about 90%, or alternatively at least about 95%, or alternatively 98% percent homology or identity and exhibits substantially equivalent biological activity to the reference protein or peptide.

As used herein the term "operatively linked" refers to the coupling of two or more molecules in a manner that does not compromise the biological function of each of the coupled molecules.

As used herein, the terms "biorecognition site" and "epitope" are used according to their ordinary meaning to describe a moiety that provides an antibody-like or antibody binding site.

Modes of Carrying Out the Disclosure

Aspects of the disclosure relate to peptide amphiphile according to the formula:

wherein:
x=Ala, His, Met, Thr, Phe, Asn, Asp, Cys, Leu
y=Ala, Val, Leu, Ile, Phe, Trp
z=Lys, Glu, Gly
c#=a linear carbon chain between 8 to 16 units in length at the N-terminus.

In some embodiments, c# is a palmitoyl moiety (c16) at the N-terminus.

The disclosed peptide amphiphile is operatively linked to a sequence, e.g. a biorecognition site or epitope. Non-limiting examples of peptide amphiphiles include:
c16-AHL$_3$K$_3$—CO$_2$H (SEQ ID NO: 3)
c16-HHL$_3$K$_3$—CO$_2$H (SEQ ID NO: 4)
c16-MHL$_3$K$_3$—CO$_2$H (SEQ ID NO: 5)

Further examples include, c16-AHL$_3$G$_3$ (SEQ ID NO: 7) operatively linked to a biorecognition site or epitope.

The peptide amphiphiles disclosed herein serve an anti-inflammatory function of heme oxygenase by incorporating an artificial heme binding site within their sequence. Not to be bound by theory, Applicants believe that the resulting peptide amphiphiles are able to promote healthy cell growth and elicit an anti-inflammatory response by binding and breaking down heme oxygenase I.

As described in the examples below, the peptide amphiphiles disclosed herein demonstrate form supermolecular structures, e.g. fibers, which bind free heme and turn off catalytic activity (FIGS. 3A-3E and FIG. 5). The sequestration of heme, in turn, renders it non-toxic. Further, preliminary data, disclosure herein, indicates that heme is decomposed once sequestered inside these supermolecular structures.

In some embodiments, the peptide amphiphile is operatively linked to a biorecognition site or epitope associated with a specific disease, disorder, or condition.

In some embodiments, the peptide amphiphile is operatively linked to a biorecognition site or epitope associated that allows for cell specificity or growth factor promotion. Non-limiting examples of such biorecognition sites and epitopes include, but are not limited to, (i) RGD(s) (SEQ ID NO: 10) which serves as a cell adhesion/integrin targeting epitope, (ii) IKVAV (SEQ ID NO: 1) that mimics laminin of the extracellular matrix to promote cell attachment and growth, and (iii) LRKKLGKA (SEQ ID NO: 2) that binds heparin sulfate that is integral in promoting angiogenesis and furthermore wound healing.

In some embodiments, the peptide amphiphile is operatively linked to a heparin binding sequence. In further embodiments, the heparin binding sequence promotes healthy vascularization.

Further aspects of this disclosure relate to uses and/or methods of administration of the peptide amphiphiles to treat or prevent one or more diseases, disorders or conditions involving an anti-inflammatory mechanism. A non-limiting example of a relevant disease, disorder, or conditions is cardiovascular disease.

Further contemplated herein are methods involving the administration of the peptide amphiphiles to stimulate wound healing, to facilitate the replacement of scar tissue, as a post-operative formulation after surgery, to facilitate the repair of tissue after myocardial infarction, and/or to stimulate the repair of necrotic tissue.

Still further aspects of this disclosure relate to compositions for use in the above disclosed methods comprising a plurality of the peptide amphiphiles and a pharmaceutically acceptable carrier. In some embodiments, the composition may be formulated for any suitable route of administration, including but not limited to injection, implantation, or application—such as but not limited to subcutaneous implantation or topical application.

The compositions disclosed herein can be administered at a dose appropriate for the given indication and the given patient. The dose for a particular subject, e.g. mammal such as a human, canine, feline, equine, caprine, bovine, etc. patient, can be readily determined by the dose used for pharmacokinetic studies. For example, a dose of between 50 to 300 µL in a mouse model of 0.5 to 3 w/v % solution can be readily converted to a suitable in vivo dose for a human.

EXAMPLES

The following examples are non-limiting and illustrative of procedures which can be used in various instances in carrying the disclosure into effect. Additionally, all reference disclosed herein below are incorporated by reference in their entirety.

Example 1

Peptide Synthesis

The peptide amphiphiles were designed to emulate naturally occurring heme active sites by re-producing the coordination environments (FIG. 6). The individual units all have the same sequence, which followed the simple design, c16-XHL$_3$K$_3$—CO$_2$H (SEQ ID NO: 8), where X represents the amino acid that is varied in this study H is the amino acid histidine, the most common heme-binding amino acid in nature (FIG. 6). These peptide amphiphiles bind heme molecules with the designed binding site XX (AA, AH, HH, or MH) are further denoted as XX in the apo state (uncoordinated heme) or XX$_{Heme}$ in the holo state (coordinated heme).

For the initial design visualization, Applicants assumed the formation of parallel β-sheets, typical for amphiphiles (FIG. 6). AH$_{Heme}$, is most similar in coordination to that of nitrophorin with a single histidine available for coordination (FIG. 6). The second peptide in the set is HH$_{Heme}$; the bis-histidine coordination is similar to neuroglobin, cytochrome b proteins (FIG. 6), (and a number of de novo designed, α-helical bundle peptides. (29, 30-34) Third, MH$_{Heme}$, was designed to offer a His-Met axial ligation similar to that found in cytochrome c. Finally, Applicants employed AA$_{Heme}$, as a control peptide to monitor any background heme activity.

These peptides produce a modest library that highlights the ability to tune heme-coordination and function within a peptide-amphiphile material through simple alterations in the primary coordination environment.

Materials and Methods

Peptide Synthesis, Purification, and Characterization. The synthetic procedure for c16-AHL3K3-CO2H (SEQ ID NO: 3) has been reported in previous studies. (10) The synthesis of c16-AAL3K3-CO2H (SEQ ID NO: 9), c16-HHL3K3-CO2H (SEQ ID NO: 4), and c16-MHL3K3-CO2H (SEQ ID NO: 5), cleavage from the resin and RP-HPLC purification followed the same strategy as the previously reported peptide. MALDI-TOF MS (Bruker UltrafleXtreme MALDI-TOF) was used to identify the peptides; c16-AAL3K3-CO2H (SEQ ID NO: 9): Calc'd for C58H111N11O10+[H+], 1122.85, found 1122.933 m/z. c16-AHL3K3-CO2H (SEQ ID NO: 3): Calc'd for C61H113N13O10+[H+], 1188.87, found 1189.006 m/z. c16-HHL3K3-CO2H (SEQ ID NO: 4): Calc'd for C64H115N15O10+[H+], 1254.90, found 1255.023 m/z. c16-MHL3K3-CO2H (SEQ ID NO: 5): Calc'd for C63H117N13O10S+[H+], 1247.88, found 1248.864 m/z, FIG. 22.

Sample Preparation. Each peptide (3-4 mg) was dissolved in nanopure water (Millipore A10) to obtain a 1 wt % solution, c16-AAL3K3-CO2H (SEQ ID NO: 9) (1 wt %, 8.9 mM), c16-AHL3K3-CO2H (SEQ ID NO: 3) (1 wt %, 8.4 mM), c16-HHL3K3-CO2H (SEQ ID NO: 4) (1 wt %, 7.9 mM) and c16-MHL3K3-CO2H (SEQ ID NO: 5) (1 wt %, 8.0 mM). Hemin (Porcine, Sigma-Aldrich) was dissolved in DMSO (Sigma Aldrich) to achieve a 10 mM stock solution. Note: He-min/DMSO stock solutions were always made to ensure that the final DMSO concentration in the sam-ple was less than 1% (v/v). Typically, 38 µL of a 1 wt % stock solution was dissolved in 260 µL of ei-ther HEPES (50 mM HEPES, 100 mM NaCl pH 7.0) or 10 mM NH4OH, pH 10.5 to yield a 1 mM sample. The samples were then heated to 65° C. for 10 minutes and cooled back to room temperature to ensure formation of the supramolecular assembly. After the sample was cooled, 3 µL of the 10 mM hemin stock solution was added to the sample to yield 100 µM hemin. The samples were again heated to 65° C. for 10 minutes and cooled back to room temperature to ensure complete heme coordination. Titration experiments analyzed samples that contained 50 µM Heme in either Hepes buffer or 10 mM NH$_4$OH. Pre-assembled peptide was added to individual solutions containing heme such that the peptide concentration ranged from 0 to 1000 µM in 50 µM increments. The samples were equilibrated at room temperature for one hour prior to UV/visible measurements. The experimental data was fit using a modified equation (see supporting online information) (56) to analyze for binding stoichiometry (n) as well as binding constant (Kd).

Microscopy. Scanning electron micrographs were obtained with a JEOL 7500 field emission scanning electron microscope equipped with a transmission electron detector. Samples of varying concentrations were dilute 100 fold in water and drop cast onto a 400 mesh copper grid with a carbon support film (Ted Pella). After 1 minute, the excess solution was wicked away and the sample air-dried. Atomic force microscopy (AFM) images were obtained with a Veeco MultiMode 8 scanning probe mi-croscope equipped with a silicon nitride tip for imaging soft-materials. The sample was prepared by drop casting 100 µL of a 200 µM (peptide) sample on freshly cleaved mica (Ted Pella) and allowed to incubate for 20 minutes. The excess sample was wicked away with filter paper and the sample dried prior to measurements.

Secondary Structure Analysis. In order to analyze secondary structural formation in the absence of heme, circular dichroism spectroscopy (Jasco, Inc. J-815) was employed to analyze the typical n-π* transitions found for a β-sheet assembly. Samples were prepared by diluting the 1 mM peptide samples described in the previous section fivefold to yield a 200 μM sample. Additional secondary structural characterization was achieved with infrared spectroscopy (Thermo Scientific, Nicolet 6700 FT-IR spectrophotometer). 10 μL of the samples described in the previous section were dropcast onto a 32 mm CaF2 plate (Sigma Aldrich) and were air dried. The thin films were aligned in the spectrophotometer and the amide I vibrations in the region from 1500-1800 $cm^{-1}$ was analyzed.

Heme Coordination. Electronic absorption spectroscopy (Cary 50 UV spectrometers) was employed to monitor the key $\pi$-$\pi^*$ transitions typical of porphyrin derived molecules. The 1 mM peptide/0.1 mM hemin samples described earlier were transferred to a quartz cuvette with a 0.1 cm pathlength window (Starna Cells, Inc.) and analyzed from 300-800 nm.

X-band continuous wave EPR experiments were carried out using a Bruker ELEXSYS E580 spectrome-ter operating in the X-band (9.4 GHz) and equipped with an Oxford CF935 helium flow cryostat with an ITC-5025 temperature controller. Samples for EPR were concentrated to 1 mM hemin and 10 mM Pep-tide with a 10,000 molecular weight cutoff spin diafiltration system (EMD Millipore Inc., Amicon Ultra-0.5 Centrifugal Filter Unit with Ultracel-10 membrane).

Electrochemistry. The samples were placed in a spectro-ecltrochemical cell (1 mm quartz) equipped with a platinum mesh working electrode, platinum wire auxiliary electrode, and a Ag/AgCl reference electrode (Basi, Inc.). The samples were electrochemically reduced over a range from +200 mV to -700 mV vs. SHE. Each applied voltage setting was allowed to equilibrate for a minimum of 20 minutes prior to UV/visible spectral acquisition (Perkin Elmer, Lambda 950, UV/vis/NIR spectrophotometer). Midpoint potential analysis was achieved by fitting a standard Boltzmann curve to the obtained data (OriginPro 9.1).

Carbon Monoxide Binding. The heme ferrous state was obtained through chemical reduction by add-ing 5 μL of a concentrated sodium dithionite (Sigma-Aldrich) solution (100 mg/mL) into a 1000 μM peptide/100 μM hemin solution (300 μL) in an eppendorf tube. All samples were equilibrated and han-dled in an inert, nitrogen atmosphere (Plas Labs Inc. 830 Series Compact Glove Box). Carbon monoxide (99.99%, Airgas) was added directly through the solution in the eppendorf tube for 30 seconds. 10 μL of the solution was dropcast onto a CaF2 plate where a CO(g) was gently blown over the droplet resulting in a thin film of the PAHeme material. The samples were than analyzed by FTIR spectroscopy (Thermo Scientific, Nicolet 6700 FT-IR spectrophotometer). The samples were stable against oxidation during the course of the experiments.

Peroxidase Activity Assay. Peroxidase activity was monitored using a Varian Cary 50 spectrophotometer and the kinetics software package. 652 nm was the chosen wavelength based on its characterization in the literature (extinction coefficient: 39,000 M−1 cm-1). In a solution of HEPES buffer, pH 7 (50 mM HEPES 100 mM NaCl), a commercially available cocktail of 3,3',5,5'-Tetramethylbenzidine (TMB) and H2O2 (both ~3 mM, purchased from Sigma-Aldrich) was diluted 1:10. This was monitored for 1 minute to detect any changes in the background then protein was added (prepared as above at 500 μM peptide and 50 μM heme) to a final concentration of 10 μM (1 μM Heme). The reaction was allowed to run for 15 minutes to assure completion. In the case of Michaelis-Menten analyses two stock solutions of TMB (10 mg/mL, 41.6 mM in DMSO) and peroxide (52.8 mM diluted in H2O, H2O2 stock concentration standardized by the method of Klassen et. al.) (57) were made so the concentrations could be varied de-pending on the experiment. When varying peroxide concentration TMB was at a concentration of 300 μM. Michaelis-Menten curves were fit using Origin 9.1 software to the equation (v0=kCat[E]0[S]0/(KM+[S]0)). Catalytic efficiency values (kCat/KM) were determined by fitting the linear portion of those curves to the equation (v0=(kCat/KM)[E]0[S]0). Total amount of oxidized TMB was calculated by integrating the absorbance at 652 nm (done with Origin 9.1 software), and dividing that value by the extinction coefficient.

Discussion

Supramolecular Characterization. To test the hypothesis that supramolecular assembly has potential to effect the coordination environment surrounding the heme, it was crucial to analyze the morphology under various conditions. Applicants found by transmission electron microscopy (TEM), atomic force microscopy (AFM), and dynamic light scattering (DLS) that the peptide-amphiphiles in HEPES buffer at pH 7 yield spherical micelles (with the exception of $AA_{Heme}$). AFM shows that the spheres are ~3-7 nm in diameter in both the presence and absence of heme (FIG. 7 and FIGS. 8A-8H). Furthermore, DLS experiments suggested ~7 nm diameter micelles in close agreement with the microscopy data, (FIG. 9). The spherical shape is attributed to the large palmitoyl (c16) tail of the peptide-amphiphiles undergoing hydrophobic collapse in concert with electro-static repulsion of the polar head group lysine residues. $AA_{Heme}$ was the only peptide to deviate from the spherical assembly where AFM, TEM, and DLS all showed fibers at neutral pH. The lack of a positively charged histidine residue at the aliphatic interior of the assembly eliminates internal electro-static repulsion allowing the formation of fibers to occur. At pH 11, the lysine head group is neutralized decreasing the effect of electrostatic repulsion where TEM and AFM show that all peptides assemble into a similar fiber morphology (FIGS. 7A-7E, FIG. 10, and FIGS. 24A-24H). AFM further showed that when heme is coordinated/embedded in the peptide fibers, they all have the same height profile, 7-8 nm (FIGS. 10A-10H).

Figure 11A:
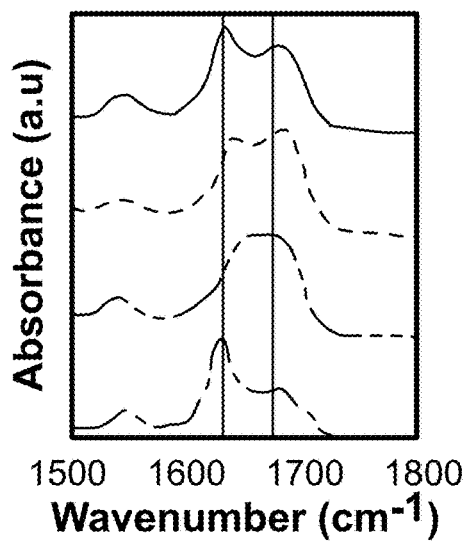
FIGS. 11A-11D are graphs of the FT-IR spectra of the amide I vibrations for AA (blue), AH (red), HH (green), and MH (purple) in a. HEPES, b. HEPES with Heme, c. 10 mM $NH_4OH$, and d. 10 mM $NH_4OH$ with Heme. The dotted vertical lines mark the expected peak positions for β-sheet values: 1630 $cm^{-1}$ and 1681 $cm^{-1}$.
Figure 11B:
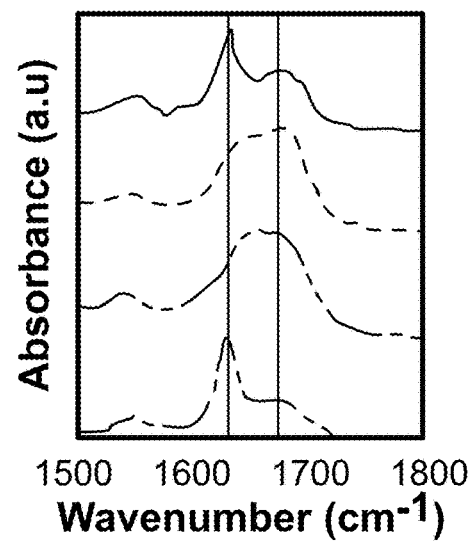
Figure 11C:
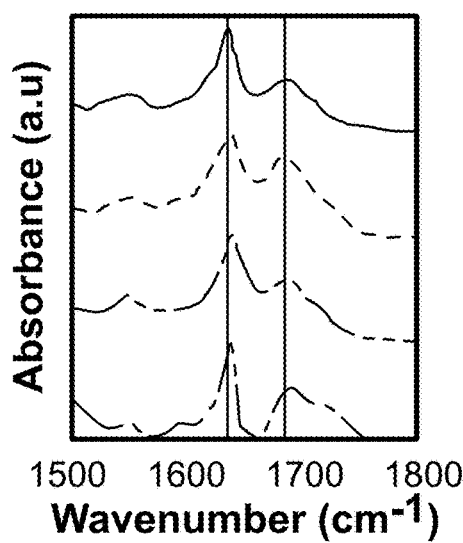
Figure 11D:
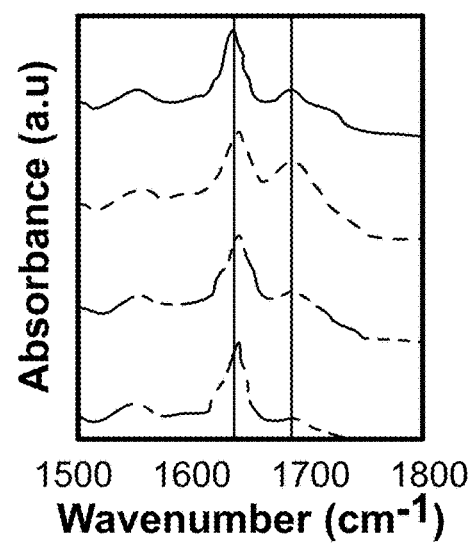
Figure 12:
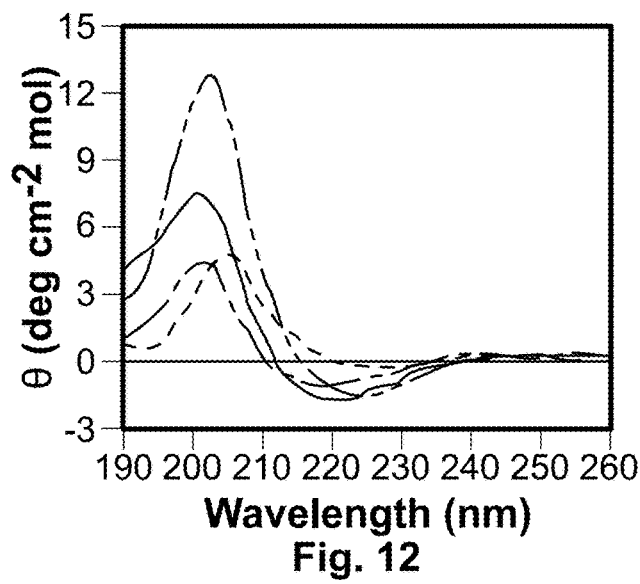
FIG. 12 is a graph of Circular dichroism spectra for $PA_{Heme}$-AA (blue), $PA_{Heme}$-AH (red), $PA_{Heme}$-HH (green), and $PA_{Heme}$-MH (purple) in 10 mM $NH_4OH$.

A relationship between morphology and secondary structure is also noted. In micelles, FT-IR analysis indicates that AH and HH lack a well-defined secondary structure whereas MH has a slight β-sheet component. AA exhibits high β-sheet content, which is often linked to fiber formation. (FIG. 11A). (35) Applicants added heme to see if the cofactor has an effect on structure; it was added at a ratio of 10 peptides: 1 cofactor to ensure maximal binding. Upon addition of heme, no significant change in secondary structure was observed (FIG. 11B) consistent with the lack of change in observed morphology. At pH 10.5, Applicants detected the formation of β-sheets by FTIR and CD, FIG. 11C and FIG. 12 respectively) with or without heme (10 peptide: 1 heme, FIG. 11D). The pKa of lysine is close to 10.5 and becomes neutralized allowing neighboring molecules to interact and form β-sheets. The CD spectra are not identical, (FIG. 12) possibly due to variations in superhelical twist that occurs during fiber formation. (36) Therefore, in the $XX_{Heme}$ series, a lack of well-defined secondary structure at neutral pH is directly correlated to spherical micelle structures whereas β-sheet formation at high pH can be directly linked to long aspect ratio fibers in bundled networks. In both micelles and fibers, the overall structure is largely unaffected by the addition of heme. As a result, a platform is developed that allows the examination of how the heme cofactor is controlled through both the primary amino acid sequence of the peptides and the supramolecular assembly.

Ferric Hemin Binding. In order to investigate the sequence and morphology effects on the heme coordination environment, Applicants employed electronic absorption (EA) spectroscopy and electron paramagnetic resonance (EPR) spectroscopy that together describe the mechanism of heme insertion, the ligand environment, and the spin state of the metal-centered cofactor, FIG. 13. The relative stoichiometry and resulting binding constants (FIG. 13E) afforded from the titration experiments indicate a dependence on the flexible micelle structures when compared to the rigid fiber structures. The results for micelles suggest a 3:1 (Peptide: Heme) stoichiometry while fibers yield a 6:1 stoichiometry (FIG. 14). Within the micelle construct, the lack of secondary structure yields a more flexible peptide environment allowing for the more favorable bis-his coordination. As a result, the highest binding affinity (lowest Kd) is simply the peptide with more available histidines, $HH_{Heme}$-$MH_{Heme}$ in micelles yields a less favorable bis-Histidine coordination environment than $AH_{Heme}$ due to some steric crowding from the bulky thioether at the heme binding site. In contrast to the favorable bis-histidine coordination environment in micelles, the β-sheet rich fibers offer a rigid structure that contributes significantly to heme binding affinity. While the $HH_{Heme}$ binding affinity is similar to that found for micelles, $AH_{Heme}$ binding affinity actually increases (lower Kd) in spite of the fact that the coordination environment is the less favorable single-histidine state (vide infra). This increase in binding affinity is promoted by the rigid fiber structure and consequently the non-bulky alanine in the "distal" position of the heme binding pocket. As a result, the opposite trend is observed in $MH_{Heme}$, where the steric crowding of the bulky methionine that was observed in micelles is amplified by the rigid system and is reflected in the decrease in heme binding affinity (increased Kd). In spite of the lack of a binding site, $AH_{Heme}$ does produce a "solubilization" curve indicating that heme is taken up by the fiber construct. This helps to explain the overall mechanism of heme insertion such that the hydrophobic heme molecule is first encapsulated by the resulting amphiphilic micelle or fiber structure. Then, if a binding site is available, the heme molecule will coordinate. The binding constant analysis determines which coordination site is the strongest, but most importantly highlights the significant influence the rigid secondary structure has over heme binding affinity.

Figure 13A:
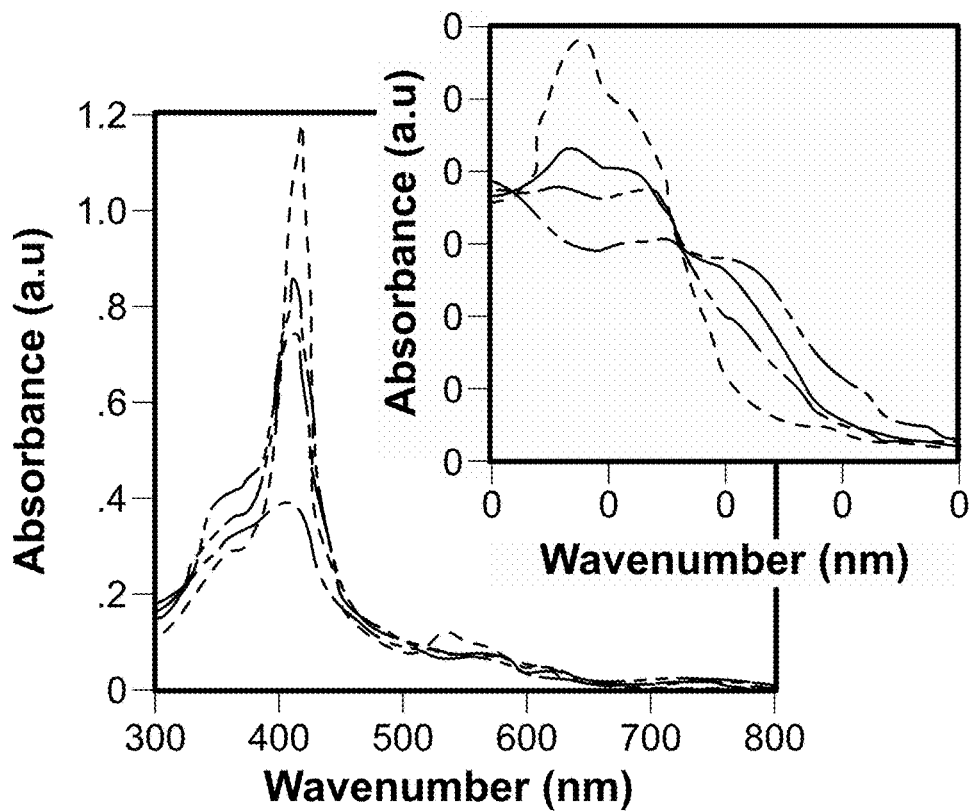
Figures 15, 16:
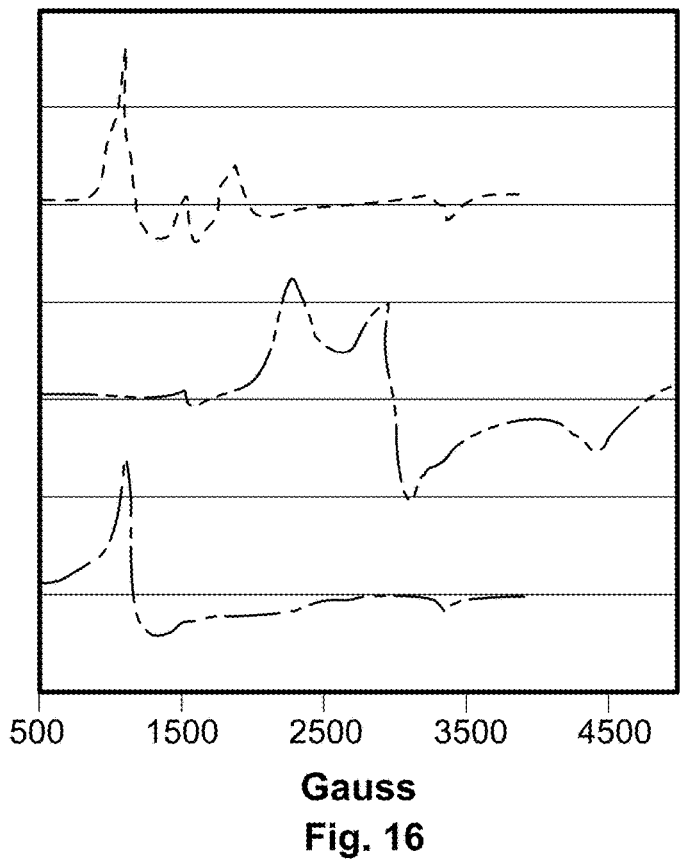
FIG. 15 is the equation employed for stoichiometry and binding constant analysis; the follow variables are used: Ao, initial absorption; εB, extinction of bound heme; εs, extinction coefficient contribution from scattering; x, ratio of peptide to heme; n, set stoichiometry of peptide to heme; Kd, dissociation (binding) constant M, molar concentration of heme; l, cuvette pathlength.
FIG. 16 is a graph of the X-band EPR spectra of hemin in 10 mM $NH_4OH$ (blue), hemin and L-Histidine (10 fold excess) in 10 mM $NH_4OH$ red), and hemin and lysine (10 fold excess) in 10 mM $NH_4OH$ (green).

For spectroscopic characterization, the Peptide: Heme stoichiometry was maintained at 10:1 to ensure complete heme coordination. In $HH_{Heme}$ micelles at neutral pH, the electronic absorption spectrum yields signature Soret and Q band values consistent with strong bis-histidine axial coordination to heme, in agreement with the spectrum for neuroglobin, (FIGS. 13A and 13E). (37) The EPR spectrum represents a purely S=½, low-spin, type II (rhombic) spin configuration, (FIGS. 13C and 13E) and is characteristic of many low-spin, bis-histidine coordinated heme proteins including neuroglobin. (38-44) $AA_{Heme}$ (fibers at neutral pH) does not offer a coordination site and therefore yields a spectrum typical of uncoordinated heme, FIGS. 13A and 13E. Free heme in aqueous solutions readily forms aggregates yielding dramatically blue shifted visible spectra from solubilized heme (FIG. 13E). (42,43) Furthermore, $AA_{Heme}$, yielded an entirely S=5/2, high-spin EPR spectrum (FIG. 13C) similar to that of free heme (FIG. 15). In $AA_{Heme}$ Applicants suspect that heme aggregation is broken up and the molecule is solubilized but not coordinated within the peptide matrix producing both the red shift in the EA spectrum (in relationship to aggregated heme) and the signature high spin spectrum from EPR, FIG. 13E.

Figure 13B:
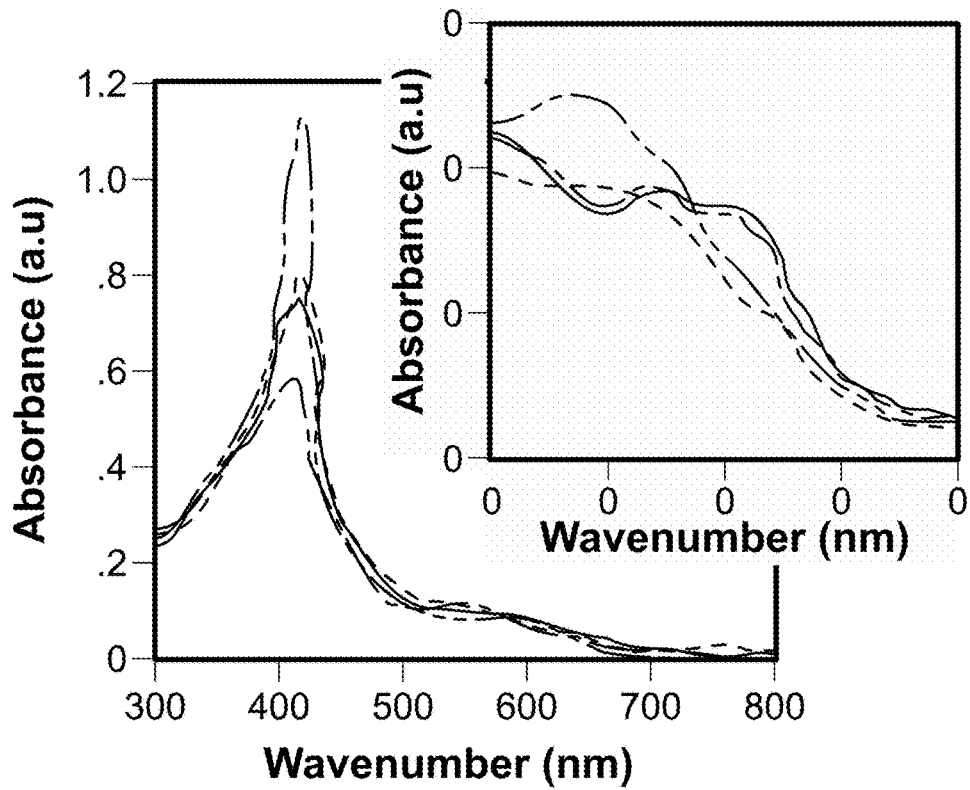
Figure 13C:
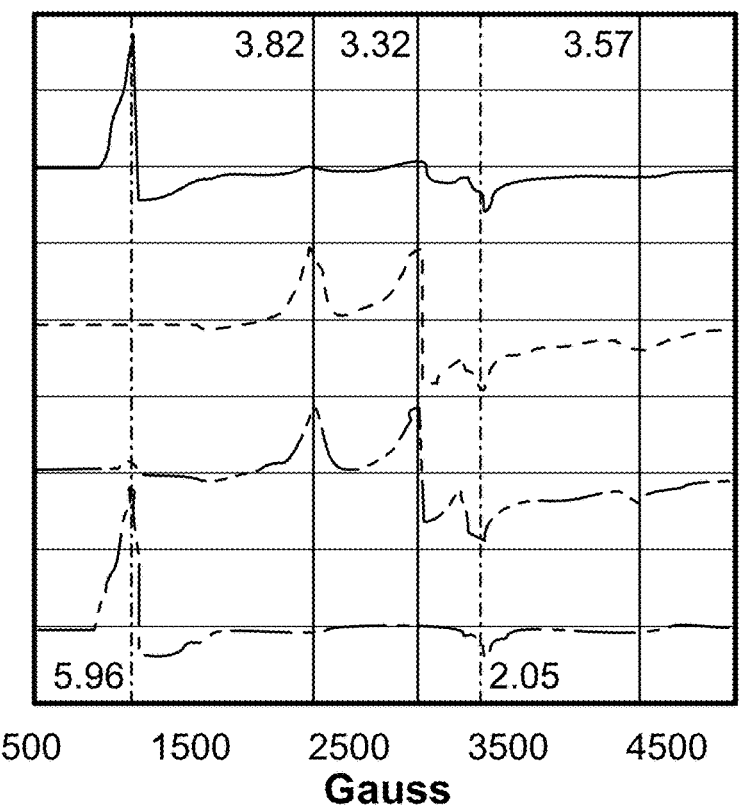

In spite of having one less histidine in its sequence than $HH_{Heme}$, $AH_{Heme}$ micelles also yield a bis-histidine heme coordination as the observed EPR spectrum is predominantly low-spin with identical g-values to $HH_{Heme}$ (FIG. 13C). On the other hand, $MH_{Heme}$ micelles yielded a mixture of coordination states: a predominantly high spin, S=5/2, EPR spectrum and an observable low-spin, bis-histidine contribution (FIG. 13C). Consistent with the EPR data, the EA spectra for $AH_{Heme}$ and $MH_{Heme}$ micelles suggest a mixture of uncoordinated and bis-histidine coordinated states (FIG. 13A). This observation is based on the changes in Soret and Q band position and intensities which represent averages between the spectra for bis-histidine heme coordination in $HH_{Heme}$ and embedded heme in $AA_{Heme}$. The presence of bis-histidine axial ligation in $AH_{Heme}$ and $MH_{Heme}$ micelles is due to the greater degree of flexibility within the micelle assembly than compared to the rigid structure of the β-sheet fibers. Thus, bis-histidine coordination in micelles occurs with any peptide-amphiphile in our series that has a histidine, e.g. $XH_{Heme}$.

Figure 13D:
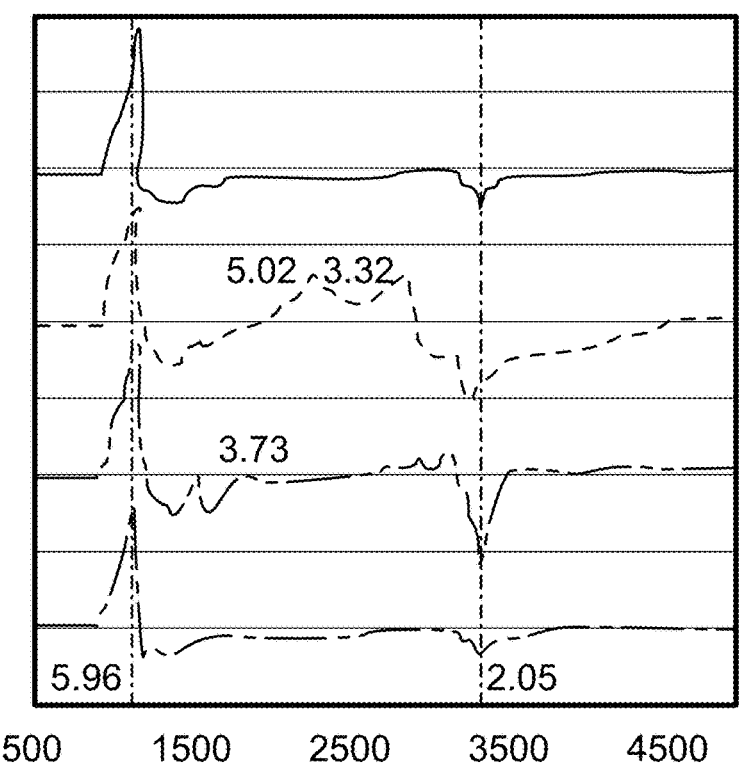
Figure 14A:
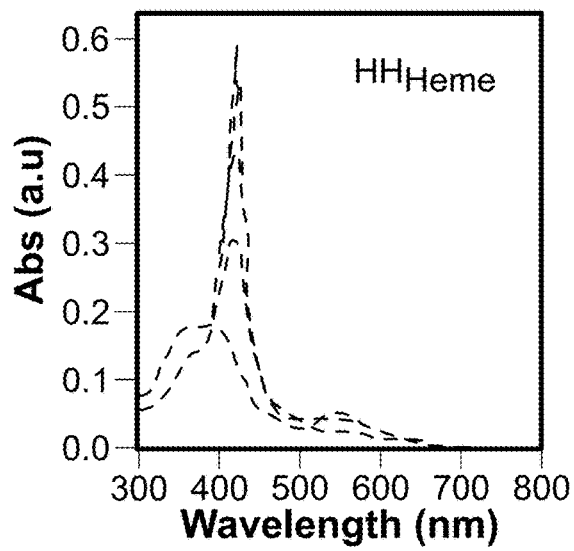
FIGS. 14A-14P depict stoichiometry and binding constant analysis of peptide titrations (0-1000 μM XX in 50 μM titrants) into heme solutions (50 μM) in Hepes buffer (right) or 10 mM $NH_4OH$ (left). UV/visible spectroscopy and plots of [Peptide]/[Heme] vs. absorption (λSoret). The solid lines represent the binding constant analysis and were obtained in Origin v9.1 by applying equation 1 (FIG. 15). The following values were fixed: $M=5\times10^{-5}$ M, $l=0.1$ cm. All other values were permitted to float for the first round of analysis. Once n was determined, a common integer was applied to each data set within the conditions employed, e.g. n=3 for HEPES and n=6 for 10 mM $NH_4OH$. The vertical line at x=10 marks the samples that were analyzed further by UV/vis and EPR. The data is reported in FIG. 13E.
Figure 14B:
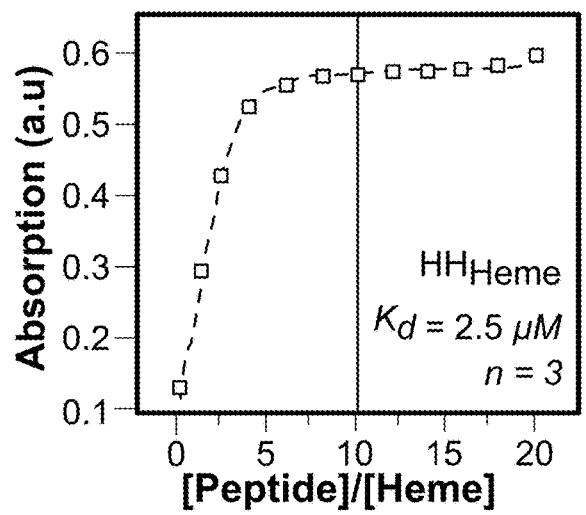
Figure 14C:
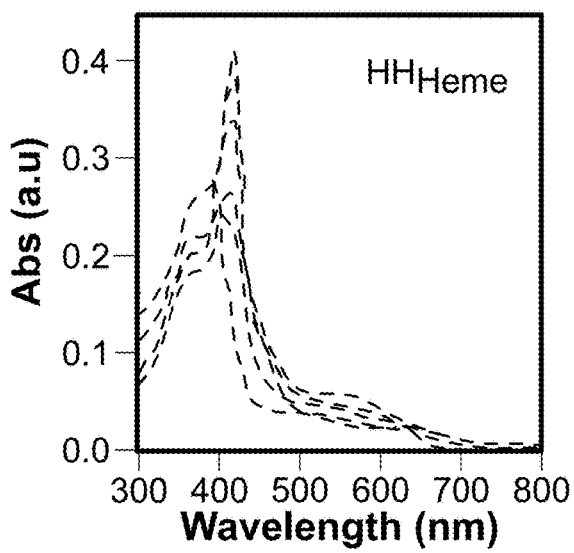
Figure 14D:
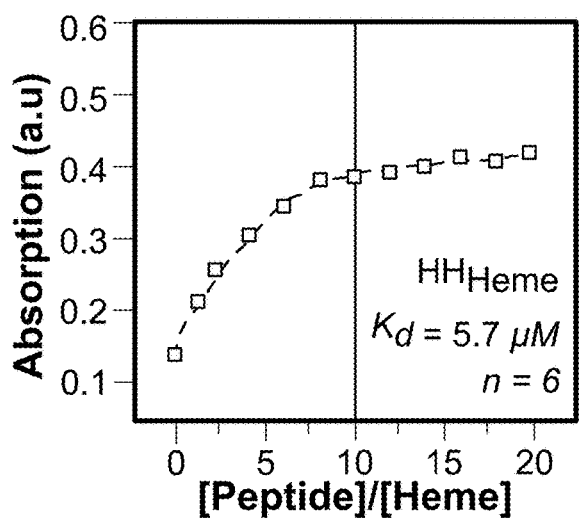
Figure 14E:
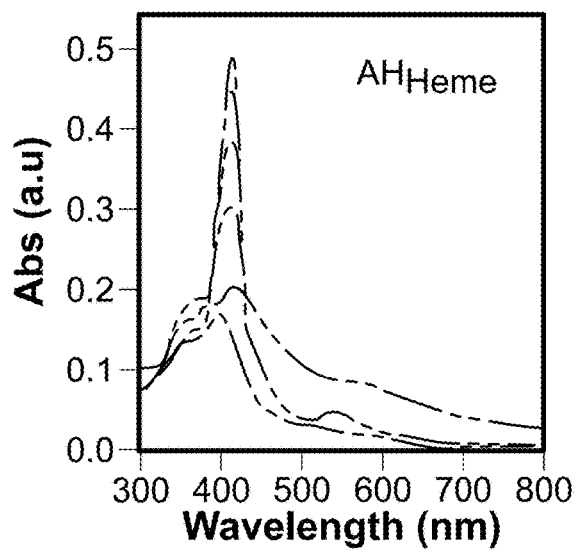
Figure 14F:
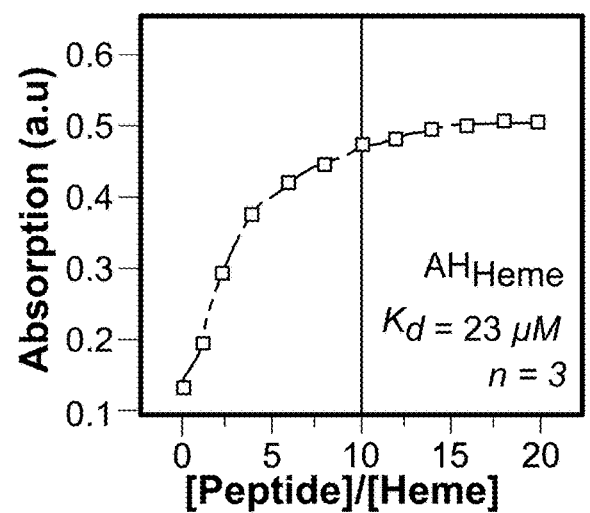
Figure 14G:
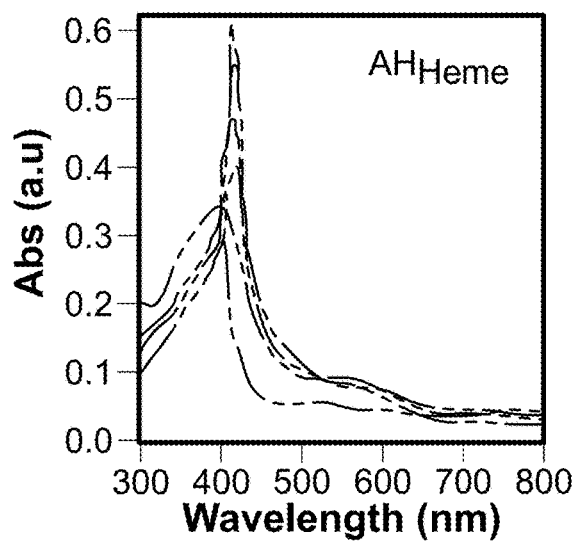
Figure 14H:
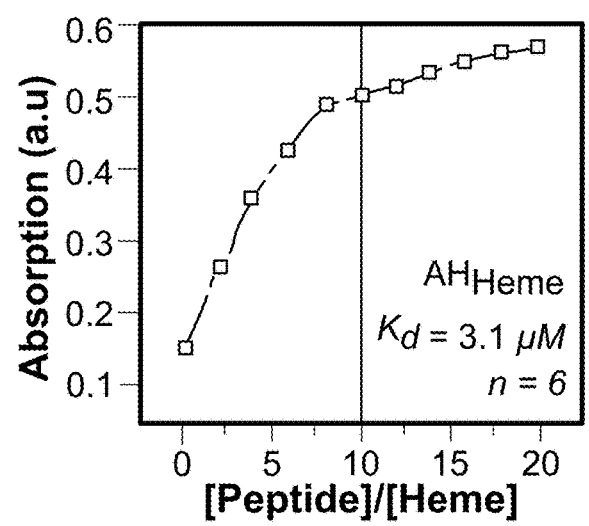
Figure 14I:
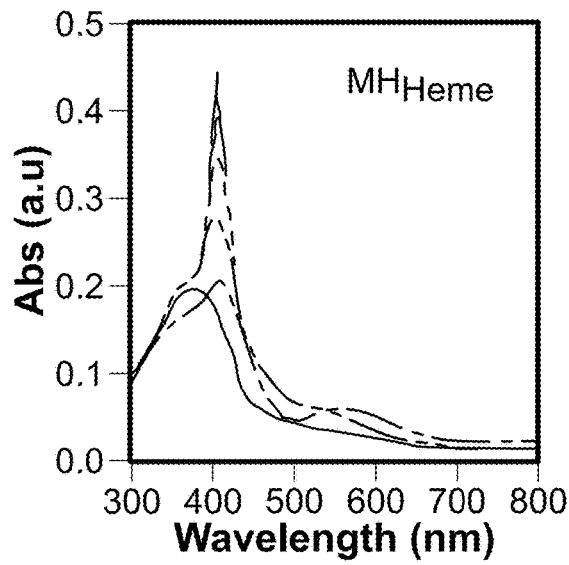
Figure 14J:
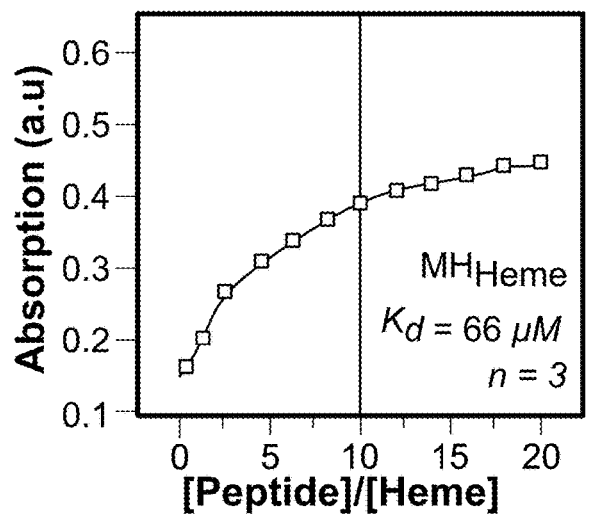
Figure 14K:
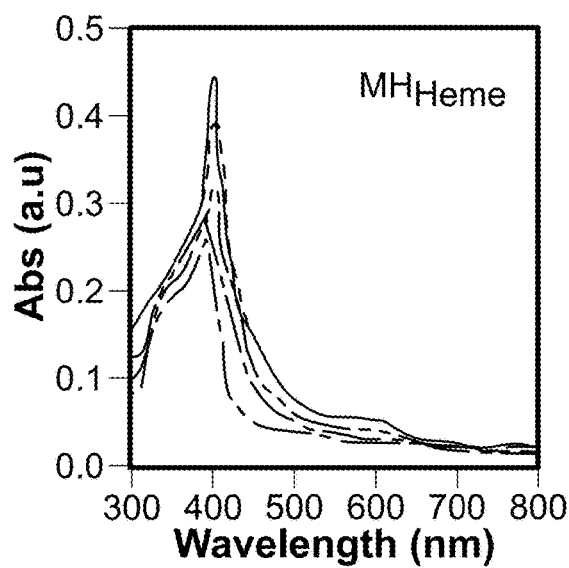
Figure 14L:
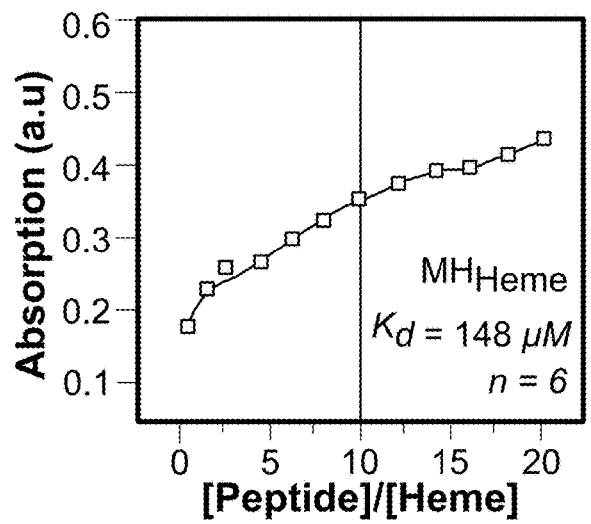
Figure 14M:
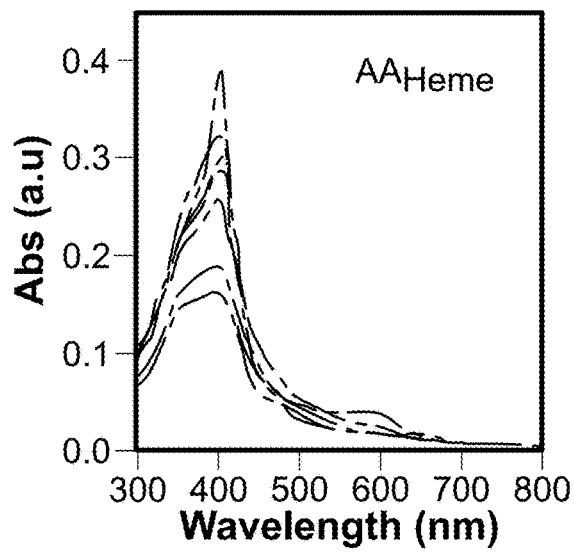
Figure 14N:
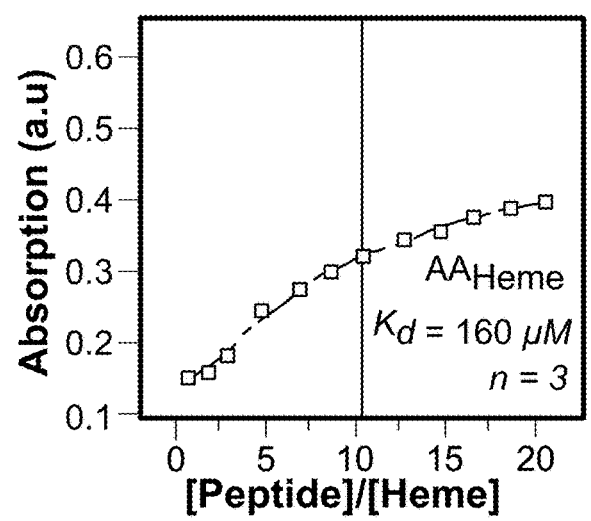
Figure 14O:
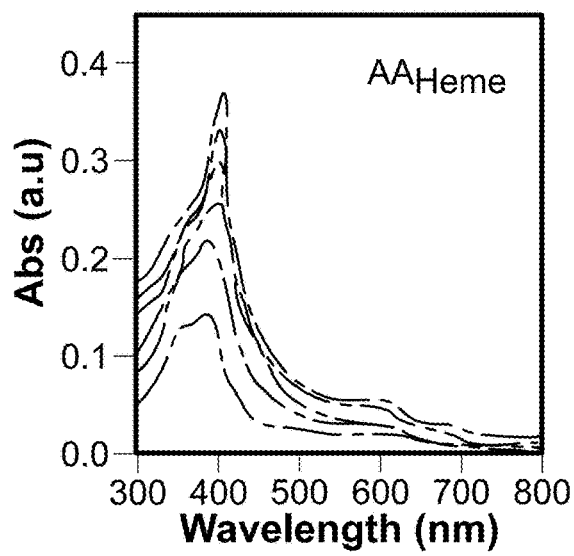
Figure 14P:
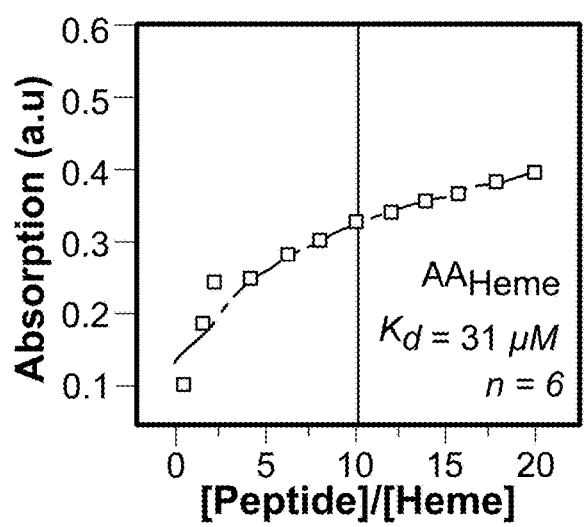

The next inquiry was how a rigid supramolecular structure affects the heme-binding site. In fibers at high pH, the electronic absorption spectra indicate unique Soret and Q bands for each peptide suggesting a variation in coordination environment from one sample to the next (FIGS. 13B and 13E). Heme coordinated to $HH_{Heme}$ fibers was shown to exhibit the same bis-histidine coordination environment as micelles as indicated by EA and EPR spectra (FIGS. 13B, 13D, and 13E). Since $AA_{Heme}$ at neutral and high pH offer the same morphology, no significant spectroscopic changes were observed (FIGS. 13B, 13D, and 13E). Applicants again suspect a lack of coordination while the heme is fixed in the matrix of the assembled fiber. Interestingly, $MH_{Heme}$ fibers yield similar spectra to that observed for $AA_{Heme}$ fibers suggesting that heme is not coordinated but embedded in the peptide assembly. This observation is further corroborated by the purely high spin EPR spectrum and is in opposition to the mixture of high and low-spin heme observed in $MH_{Heme}$ micelles. It should be noted that cytochrome c which coordinates heme through histidine-methionine ligation, yields a low spin, type I, highly anisotropic low spin (HALS) spectrum with a g value ~3.3 further suggesting that the desired histidine-methionine coordination was not achieved in $MH_{Heme}$, (FIG. 6). (44) Applicants attribute the lack of heme coordination to the in-creased molecular ordering (i.e β-sheets) within the assembly where the bulky methionine residue sterically blocks heme access to the histidine coordination site. Finally, heme coordinated to $AH_{Heme}$ fibers yields an EA spectrum indicative of coordinated heme but not typical of bis-histidine axial ligation as it is blue shifted to a value similar to that of nitrophorin which possesses single histidine axial ligation (FIGS. 13B and 13E). The EPR spectrum shows a predominantly high spin species as expected for single histidine axially coordinated heme like nitrophorin. (41, 45) The value observed at $g_z$=3.71 is typical of a low-spin type I (HALS) spectrum and is observed in our control experiment where heme is analyzed in the presence of lysine (FIG. 16). (40) Applicants conclude that the observed spectrum for heme coordinated to $AH_{Heme}$ fibers is predominantly a high-spin spectrum representative of a single histidine-coordinated heme with some propensity for unresolved low-spin states.

The EA spectra and EPR data found for heme coordination to the $XH_{Heme}$ series highlights a strong link between peptide sequence, molecular ordering, morphology, and heme coordination. $HH_{Heme}$ highlights our ability to design a peptide that maintains bis-histidine coordination when converting from micelles to fibers. $MH_{Heme}$ indicates that the histidine residues available for heme coordination in a mi-celle are effectively blocked by the bulky methionine side chain upon the ordering/formation of β-sheet rich fibers. Finally, $AH_{Heme}$ highlights a change in coordination environment that can be linked to a morphological shift from (1) micelles yielding low-spin, bis-histidine coordination to (2) high density β-sheet containing fibers providing high spin, single histidine axial ligation. These pH dependent changes serve as highly programmable features for the development of functional heme peptide materials.

Figure 17A:
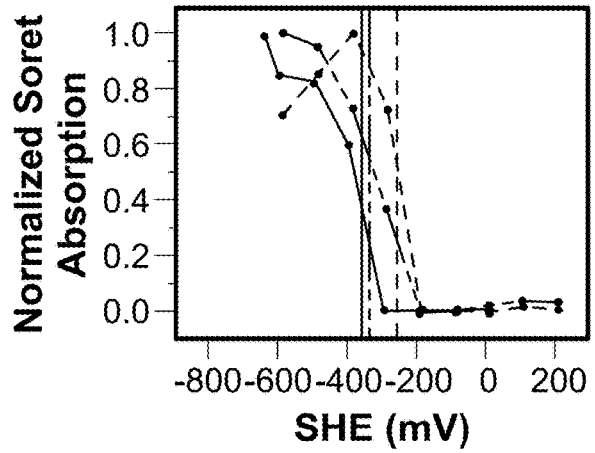
FIGS. 17A-17B are spectroelectrochemical data (applied voltage in mV versus absorption intensity (a.u.) at the Soret band maximum) of $PA_{Heme}$-AH (red), $PA_{Heme}$-HH (green), and $PA_{Heme}$-MH (purple) in HEPES (right) and 10 mM $NH_4OH$ (left). Vertical dashed lines mark the midpoint potentials disclosed herein.
Figure 17B:
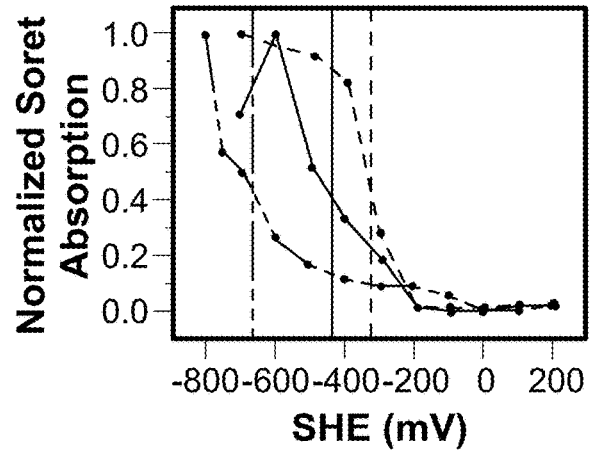

Electrochemistry. Redox behavior is another aspect where the binding site exerts control over heme in both natural and de novo proteins. (14 30,31,46) Disclosed herein is the ability to change the redox behavior of heme in the disclosed peptide materials through sequence and structure. In micelles, where the peptides exhibit similar coordination environments, $AH_{Heme}$, $HH_{Heme}$, and $MH_{Heme}$ all exhibit similar midpoint potentials ($E_M$) vs. SHE: −315 mV, −270 mV, and −312 mV respectively (FIG. 17). When the same samples were analyzed as fibers the trend changed, $AH_{Heme}$, $HH_{Heme}$, and $MH_{Heme}$ all exhibit very different $E_M$ values vs. SHE: −655 mV, −333 mV, and −442 mV respectively (FIG. 17). Applicants attribute these results to the established variation in coordination environment between the micelle and β-sheet rich fibrous morphologies. For example, there is negligible change in coordination state between $HH_{Heme}$ in micelles vs. fibers, which extends to a minimal change in $E_M$, but $AH_{Heme}$ yields a dramatic change that we attribute to different coordination modes, bis-histidine in micelles versus single-histidine in the β-sheet fibers.

Gas Binding. Heme enzymes often bind and transport small molecules like water, dioxygen ($O_2$), or nitric ox-ide (NO) using coordination bonds. Each of these small molecules plays a vital role in signaling and when combined with the well-established properties of peptide amphiphiles produces multivariate functional materials that could be used in vasodilation (NO), (47), neurotransmission (NO & CO), (48,49), and $O_2$ delivery or activation. (50,51) Applicants chose to explore carbon monoxide (CO) gas binding because CO serves as a redox inactive surrogate to these gases binding to ferrous ($Fe_{2+}$) heme where (1) it offers major insight into small molecule accessibility of the $XH_{Heme}$ active site relevant to enzymatic activity and (2) provides information on how the peptide sequence can affect gas binding. (52) Infrared spectroscopy is employed because the heme binding pocket and ligand coordination directly influence the vibrational frequency of CO ($v_{CO}$) either through enhanced backbonding or ligand coordination enhance-ment/disruption as indicated in the wide range of observed stretching frequencies, $v_{CO}$=1949-1971 $cm^{-1}$, FIG. 18. (52)

For micelles at pH=7, $AH_{Heme}$, $v_{CO}$=1967 $cm^{-1}$; $HH_{Heme}$, $v_{CO}$=1963 $cm^{-1}$; and $MH_{Heme}$, $v_{CO}$=1969 $cm^{-1}$ yield similar values (FIG. 18) due to their similar coordination environ-ments consistent with EAS and EPR. These values are notably higher than values obtained for the analogous coordination environment of myoglobin, (52) $v_{CO}$=1947 $cm^{-1}$ likely because micelle assembly lacks the more sophisticated structure of a fully folded protein. Mutations to various residues in the myoglobin active site result in an observed decrease in CO-heme backbonding, evidenced by an increase in stretching frequencies, (52), $v_{CO}$=1965-1971 $cm^{-1}$, consistent with the measured values here. In the case of $AA_{Heme}$ where fibers are formed regardless of environment and no discernible coordination is observed, two vibrational states were found, $v_{CO}$=1951 $cm^{-1}$ and 1970 $cm^{-1}$, with the former contributing the larger fraction of the peak.

Figure 18A:
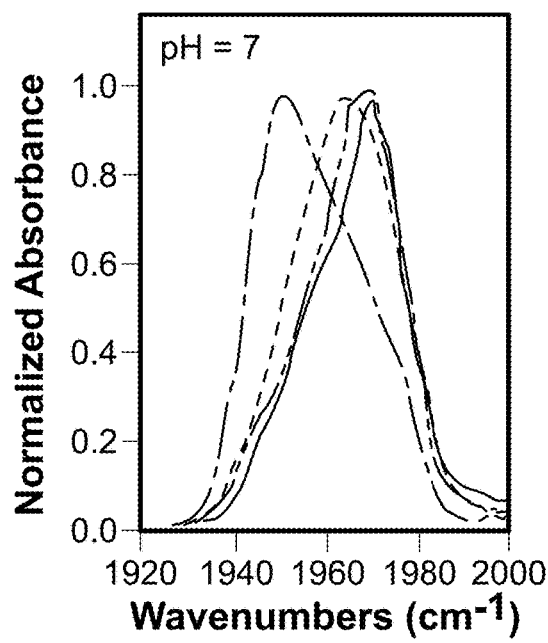
FIGS. 18A-18B show carbon monoxide vibrational analysis probing enzymatic capability and molecular structure. Infrared spectros-copy of heme-CO binding in the CO stretching frequency region at pH=7 and pH=10.5. $AA_{Heme}$, Blue; $AH_{Heme}$, Red; $HH_{Heme}$, Green; $MH_{Heme}$, Purple. Hemin, 100 μM; Peptide, 1 mM.
Figure 18B:
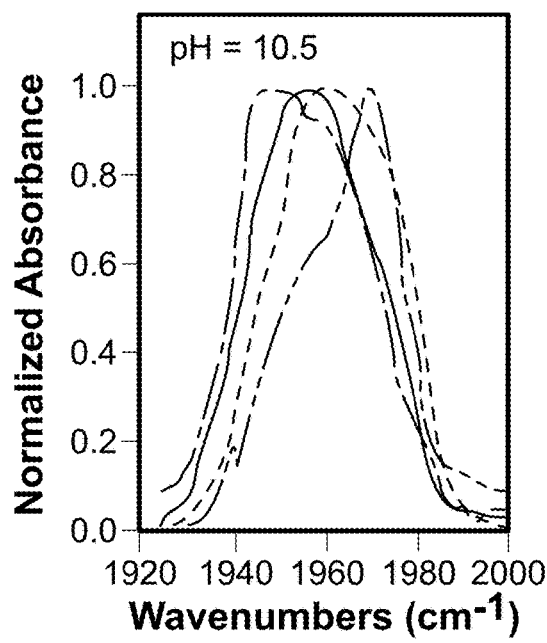

Interestingly with $XX_{Heme}$ fibers, which we have shown to greatly influence the coordination environ-ment of ferric heme, we observe different CO vibrational frequencies for each assembly (FIG. 18). In the case of $HH_{Heme}$, we assume one of the histidine ligands becomes uncoordinated allowing CO binding to occur, yielding a distal histidine similar to that found in myoglobin. Again, the value obtained for $HH_{Heme}$, $v_{CO}$=1961 $cm^{-1}$ is higher than values obtained for myoglobin, but it is slightly lower than the value obtained for the micelle conformation. We suggest that a slight increase in backbonding is generated in the fiber assembly due to the presence of a distal histidine in a more rigid environment. When we produce a similar coordination environment to the distal-site mutants of myoglobin (e.g. His→Ala) we observe an increase in stretching frequency for $AH_{Heme}$, $v_{CO}$=1970 $cm^{-1}$, slightly greater than that found in the micelle structure for $AH_{Heme}$. This is likely due to the lack of secondary structure in the micelles allowing unco-ordinated histidine residues to interact with the heme-CO complex in the pocket yielding a slightly lower $v_{CO}$. Therefore, in the β-sheet enriched fibrous assemblies, a more rigid aliphatic distal site is produced yielding the observed increase in vibrational frequency. It is interesting to note that, $MH_{Heme}$ does not appear to coordinate heme in the ferric state but CO vibrational analysis of $MH_{Heme}$, $v_{CO}$=1957 $cm^{-1}$, suggests heme coordination in the ferrous state as there is a noted difference with the value obtained for uncoordinated heme in $AA_{Heme}$, $v_{CO}$=1949 $cm^{-1}$. Furthermore, the largest change in $v_{CO}$ with respect to change in morphology from micelles to fibers is observed in $MH_{Heme}$ with an overall $\Delta v_{CO}$=12 $cm^{-1}$ further supporting our claim that there is a clear difference in coordination environment dictated by the morphology of the supramolecular assembly. Thus, Applicants have demonstrated a material capable of binding gases with varying affinity based on sequence and morphology. The changing characteristics of the porphyrin cofactor in the core hold the promise for a material that can transport and release gas based on environmental triggers.

Supramolecular Control of Enzymatic Activity.

Figure 19A:
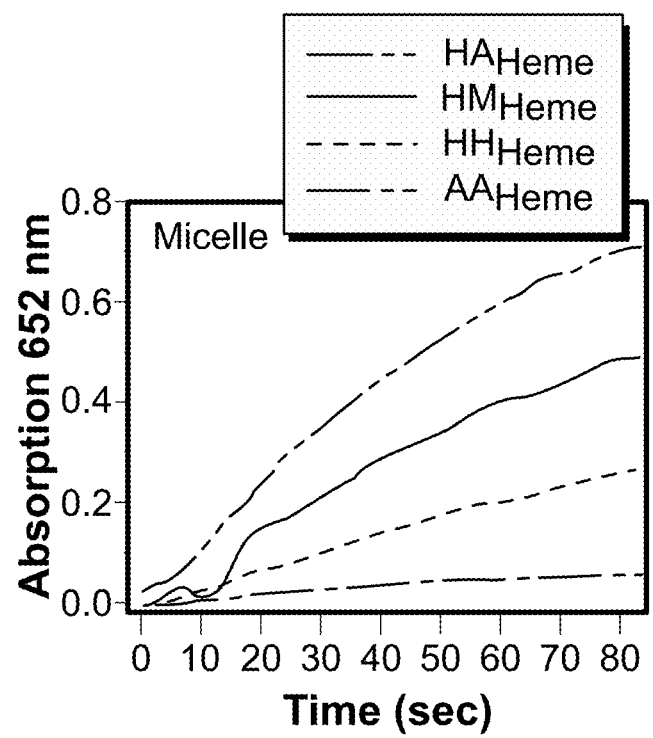
Figure 19B:
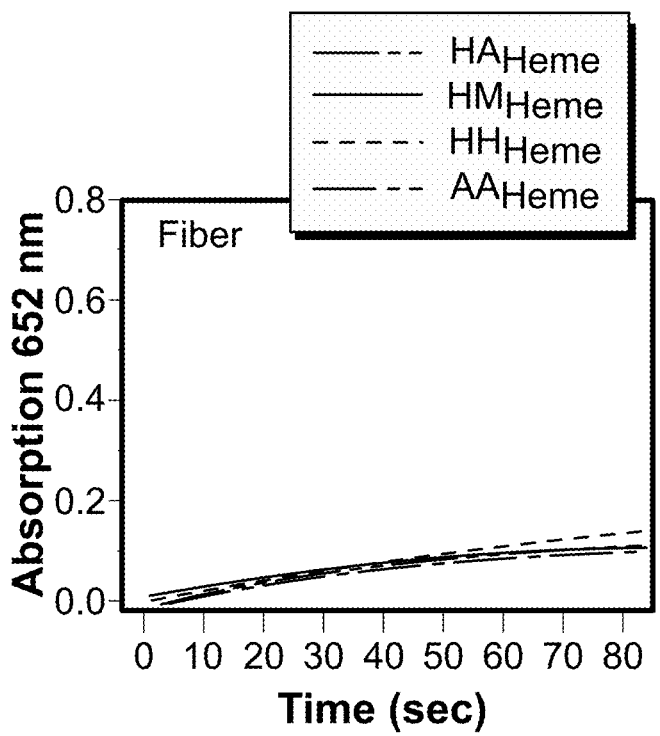
Figure 20A:
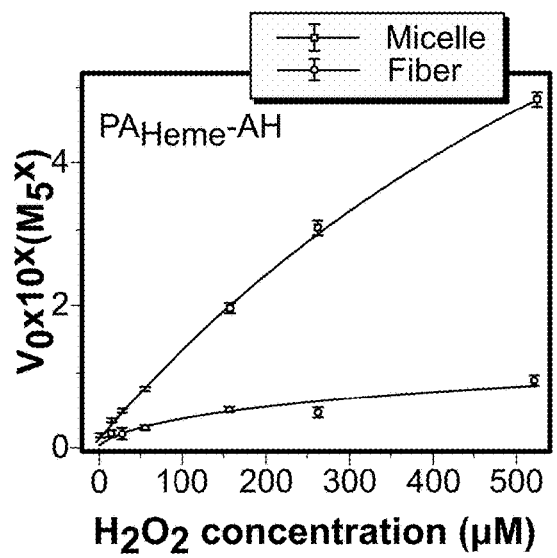
FIGS. 20A-20D show Michaelis-Menten curves examining peroxidase activity for the four peptide-amphiphiles discussed in this manuscript. For all experiments TMB: 300 μM, Peptide: 10 μM, Heme: 1 μM, HEPES buffer pH 7.
Figure 20B:
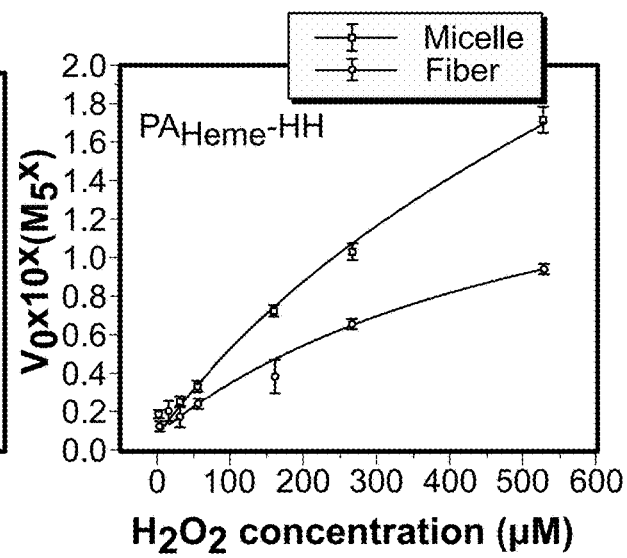
Figure 20C:
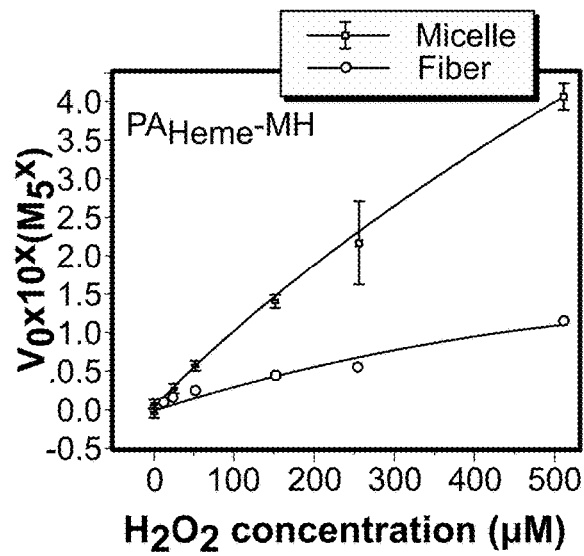
Figure 20D:
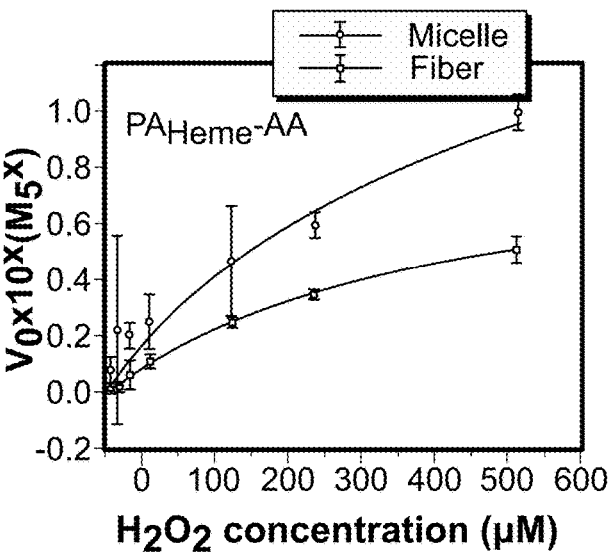
Figure 21A:
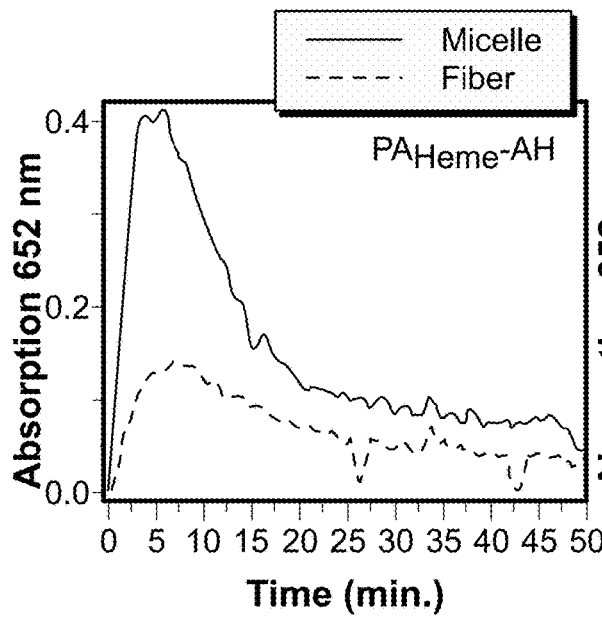
FIGS. 21A-21D are the results of peroxidase assays for the library of peptides run over extended times. $PA_{Heme}$-AH and $PA_{Heme}$-MH have the most initial activity, but stop oxidizing TMB before $PA_{Heme}$-HH does. As before $PA_{Heme}$-AA does not appear to have any activity even in this expanded time-window. For all experiments TMB: ~300 μM, H2O2: ~300 μM (diluted 1:10 from stock purchased from Sigma-Aldrich) Peptide: 10 μM, Heme: 1 μM, HEPES buffer pH 7.
Figure 21B:
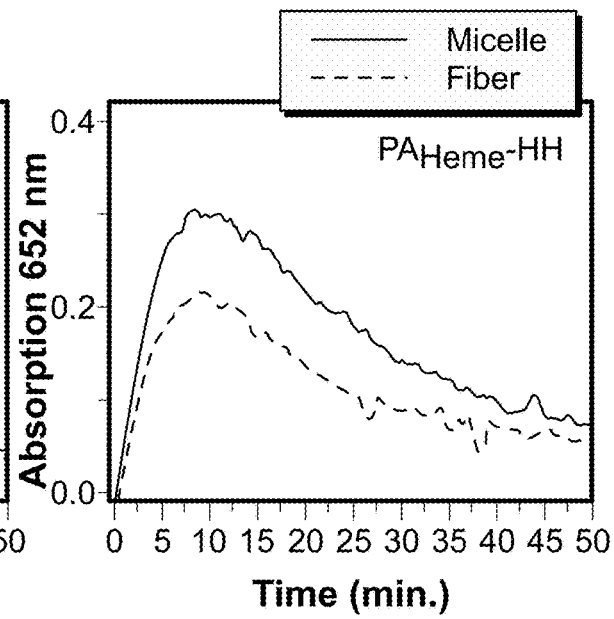
Figure 21C:
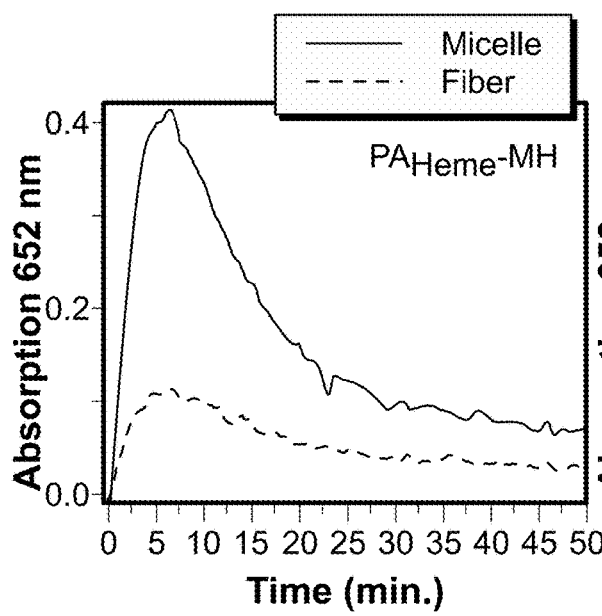
Figure 21D:
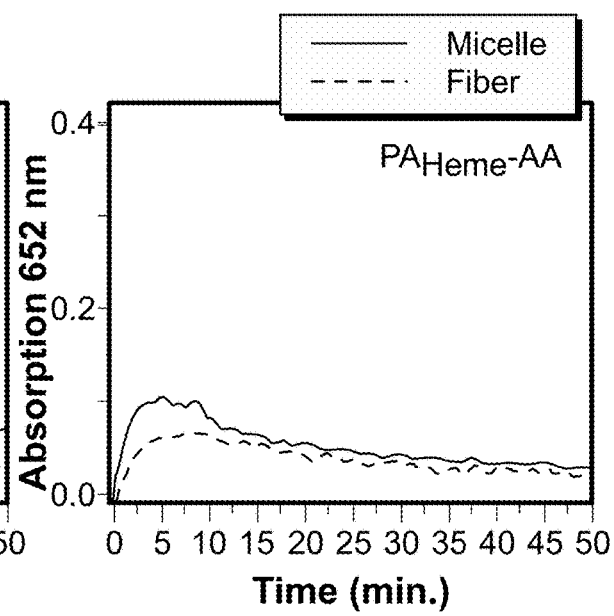
Figure 22A:
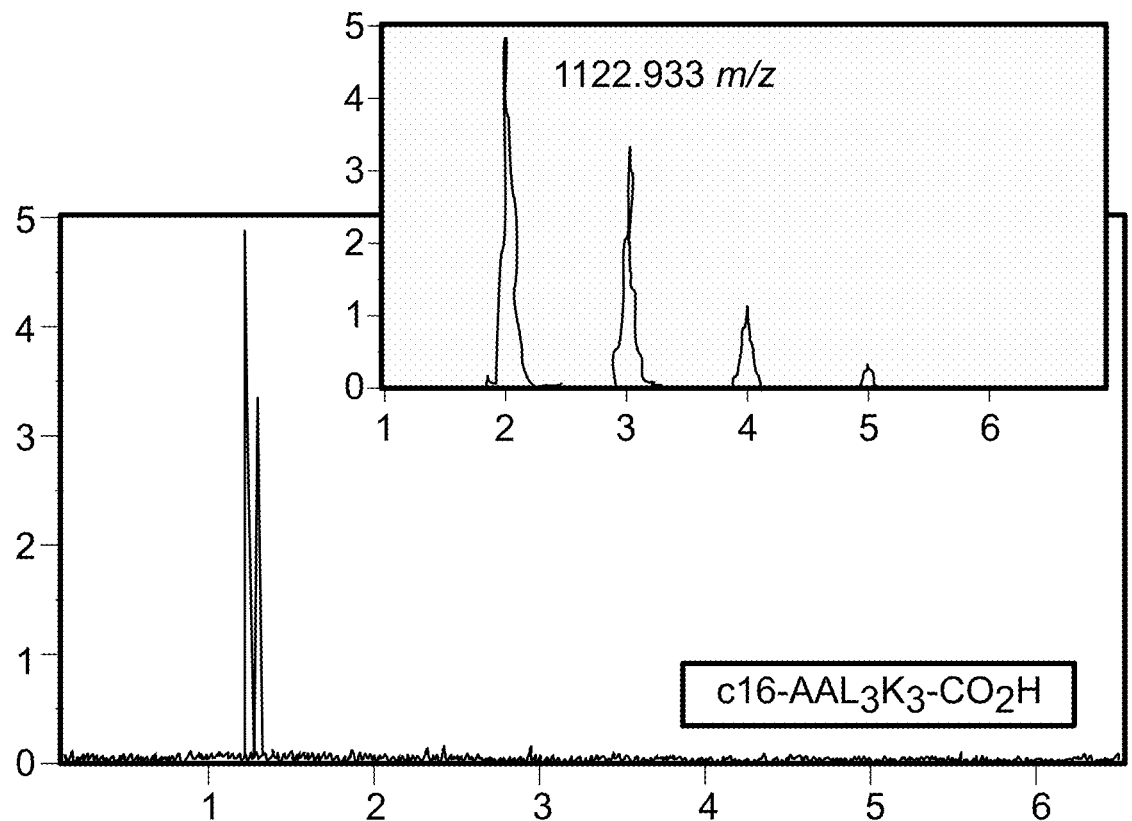
FIGS. 22A-22H depict MALDI-TOF mass spectroscopy of the peptide amphiphile series (SEQ ID NOS: 9 and 3-5, respectively, in order of appearance).
Figure 22B:
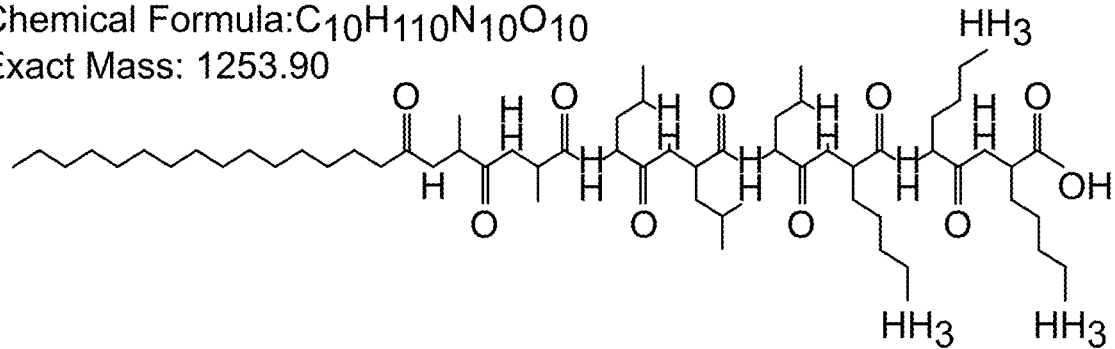
Figure 22C:
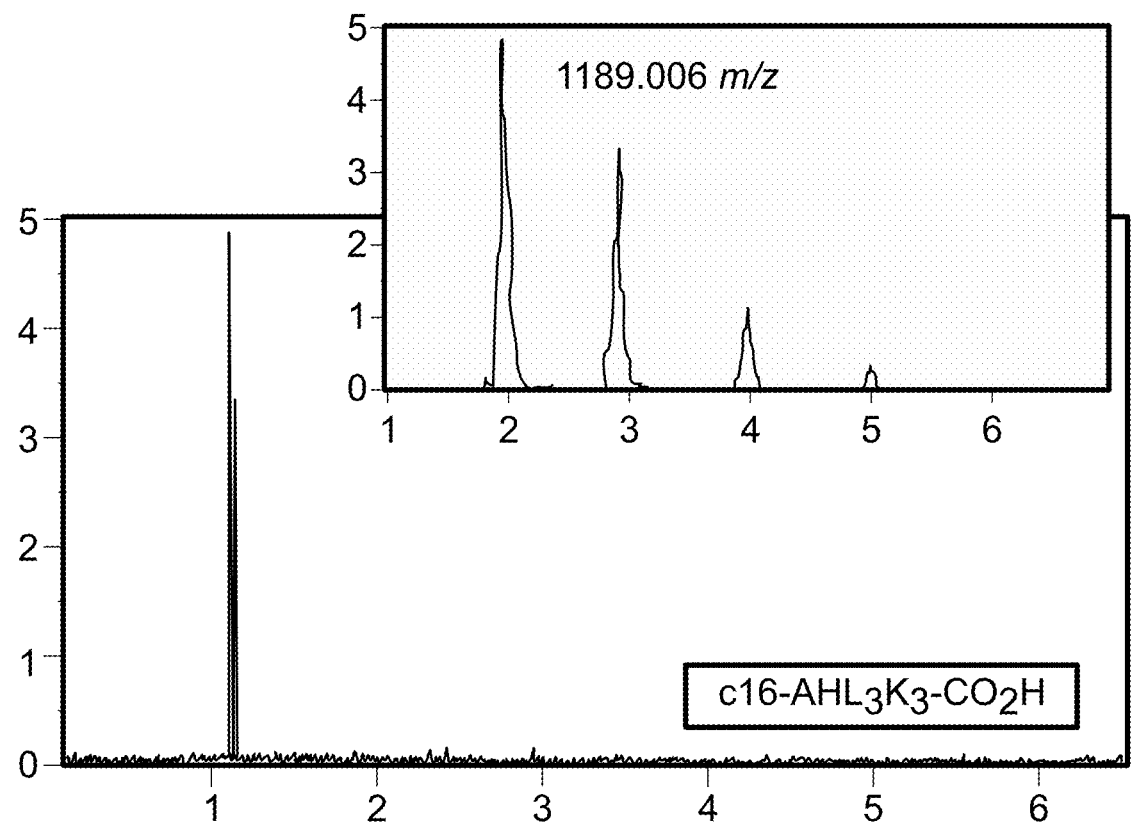
Figure 22D:
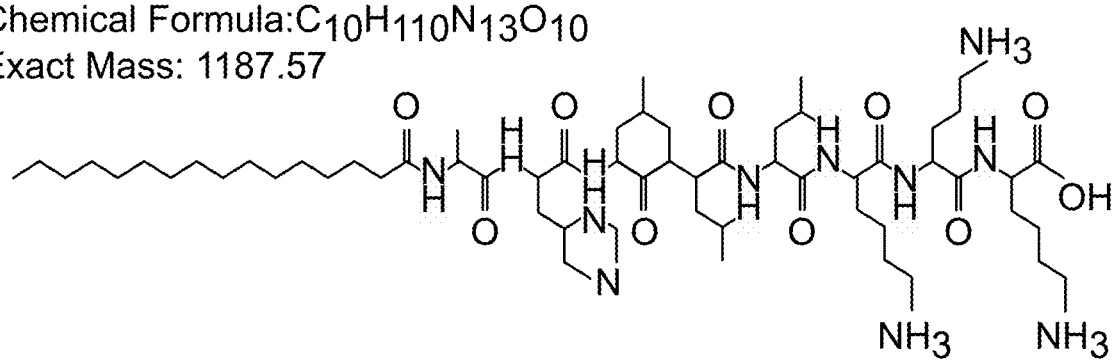
Figure 22E:
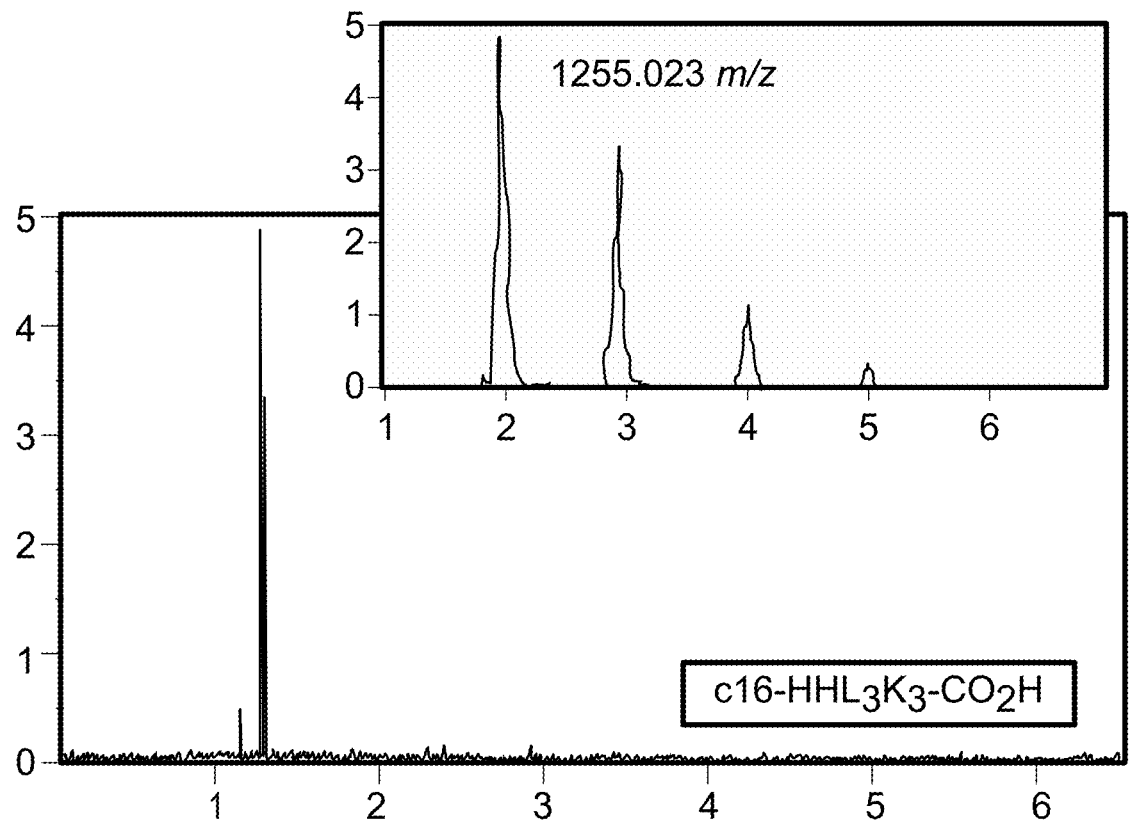
Figure 22F:
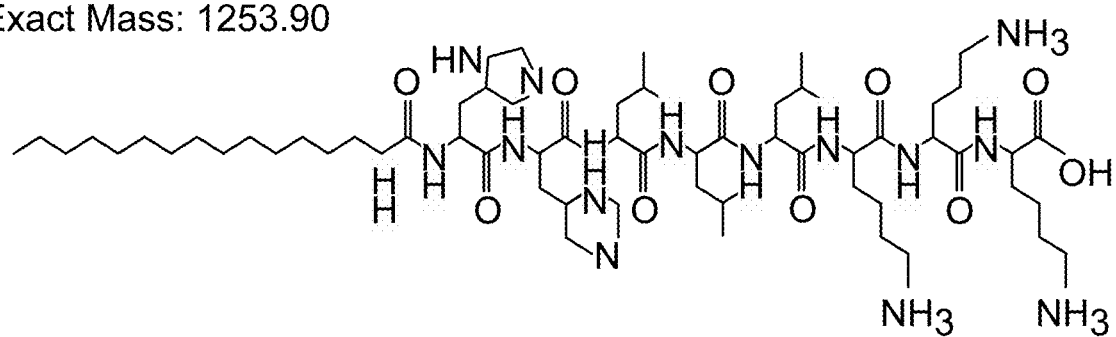
Figure 22G:
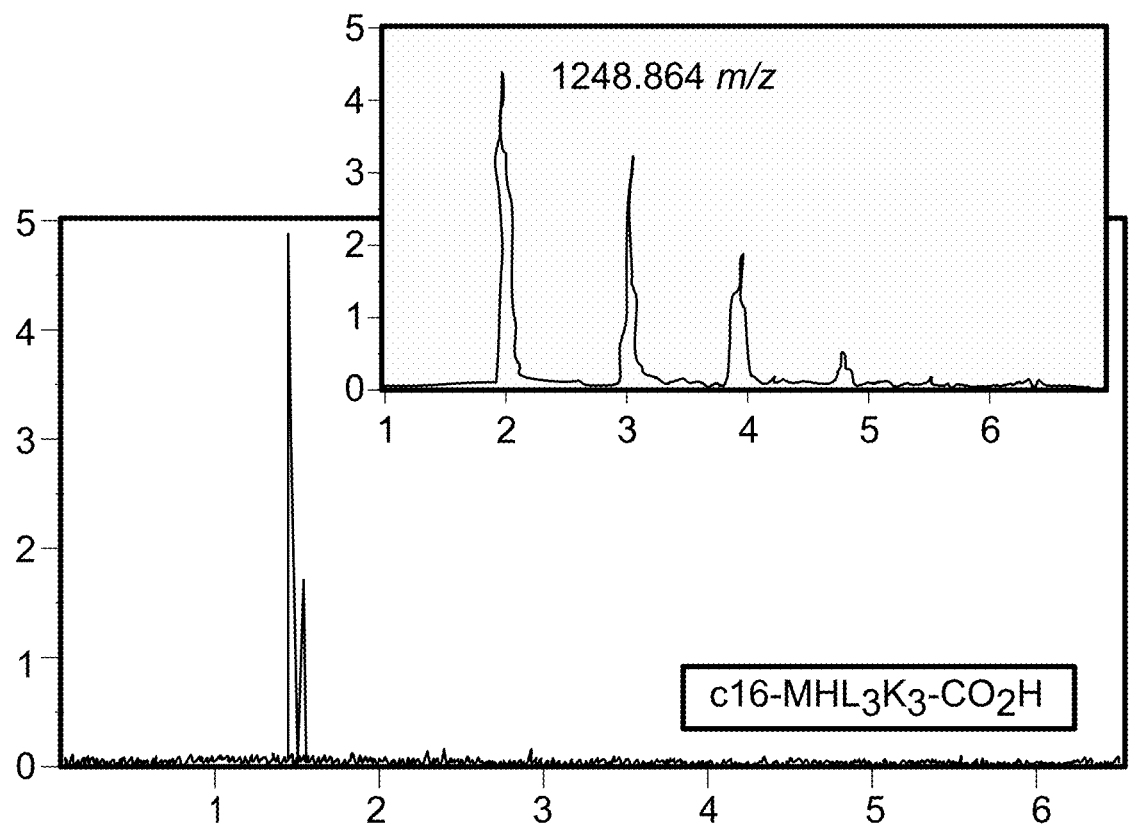
Figure 22H:
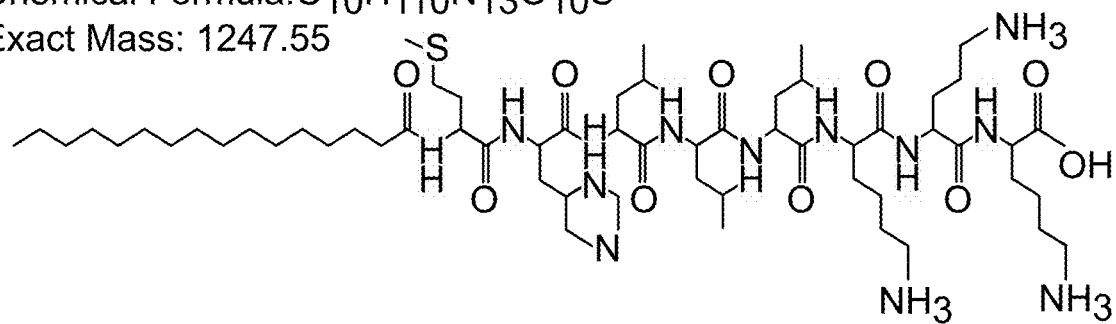

Many natural and synthetic heme proteins display per-oxidase activity, a natural reaction that catalyzes the oxidation of high potential substrates using hydrogen peroxide ($H_2O_2$). Here, we employed heme-peroxidase catalysis as a benchmark reaction to investigate how supramolecular morphology in PA-Heme assemblies can control catalytic reactivity. (53) We have chosen the established protocol where $H_2O_2$ activated by the $XX_{Heme}$ assemblies reacts with the colorless molecule 3,3',5,5'-tetramethylbenzidine (TMB) to yield the oxidized blue diimine product and water. (54) All of these assays were carried out in pH 7 HEPES buffer. Peptide assemblies were prepared in either pH 7 HEPES or 10.5 $NH_4OH$ and then diluted 50 fold into the reaction mixture to maintain standard reaction conditions. For micelles, there is a significant amount of enzymatic activity when the peptide displays histidine for heme coordination. As expected, the peptides $AH_{Heme}$, $HH_{Heme}$, and $MH_{Heme}$, exhibit varying degrees of bis-histidine coordination, and exhibit varying degrees of peroxidase activity, whereas $AA_{Heme}$ is not reactive (FIG. 19A). The rates of these peptides are consistent with the Michaelis-Menten enzyme kinetics model (FIGS. 19C, 19D, and 21). Interestingly, the samples prepared in 10 mM $NH_4OH$ as fibrous assemblies and then diluted into HEPES buffer so they maintain their morphology, appear to have lost al-most all peroxidase activity (FIG. 19B). Applicants show a clear and significant dependence of peroxidase activity dependent on supramolecular morphology. This indicates that the more rigid and densely packed fiber structures inhibit the peroxidase activity, likely by limiting access of either TMB or $H_2O_2$. The micelle structures offer a more dynamic assembly that allows substrate to interact with the engineered heme active site. By changing the morphology, and by extension the coordination environment, of the peptide-amphiphile assembly we demonstrate a significant effect on catalytic activity of the heme.

Not only is peroxidase activity dependent on the supramolecular structure, but the sequence of the peptide exerts control as well. Interestingly, $HH_{Heme}$ in micellar form appears to have low reactivity compared to the other peptides (FIGS. 19A and 19D). This could potentially be a result of restricted heme ac-cess for $H_2O_2$ due to the higher local concentration of histidine ligating to heme. However, at longer timescales, it appears able to catalyze a similar amount of TMB oxidation as $MH_{Heme}$ and $AH_{Heme}$, suggesting that while the $k_{Cat}$ and $k_{Cat}/K_M$ may be lower the stability is not affected (FIGS. 19D, 22, and 23). The presence of a low-spin heme appears to aid reactivity, as all peptides that do not have this EPR signal are inactive. However, $MH_{Heme}$ has a higher $k_{Cat}$ than $HH_{Heme}$, but a significantly weaker low-spin signal indicating low-spin heme is not solely responsible.

Applicants have demonstrated the ability to control heme coordination and function through peptide sequence design and supramolecular structure. Morphological control is exhibited through changes in buffer choice and pH, e.g. micelle and fiber assemblies can be formed. We have highlighted that different heme coordination environments with varying affinities are observed depending on the morphology and primary sequence/designed-binding site. Namely, $AH_{Heme}$ complexes where the micelle conformation yields low-spin, bis-histidine ligation but the fiber yields high-spin, single-histidine coordination. With regard to eliciting function, we have highlighted the ability of the material to coordinate the redox surrogate small molecule, carbon monoxide, which highlights the ability of the heme to bind and potentially transport molecules crucial to neurotransmission, vasodilation, and $O_2$ transport. Finally, we have found a strong influence of supramolecular assembly in which the fibers turn off and micelles turn on peroxidase activity. The catalytic activity in micelles exhibit a slight dependence on the primary sequence with $AH_{Heme}$ displaying highest catalytic efficiency, most likely due to its uncompromised and open active site. The function of the heme is crucial to producing advanced peptide materials will be explored in future work where studies on more complex assemblies are underway.

This peptide-amphiphile system provides multiple avenues with which to control potential enzymatic activity that can ultimately be translated to the material's functional properties. Sequence can be used to slow the rate, while gross structure can act as an on/off switch allowing for tuning of the reactivity as a function of environment. These results significantly impact molecular design strategies for functional peptide materials where we have discovered that supramolecular structure plays an essential role dictating heme function. For example, we will investigate fibrous structures that have potential use in anti-inflammatory signaling where the peptide assembly could be employed to sequester and break down toxic free-heme, resulting from sustained injuries (similar to the protein heme oxygenase I) while simultaneously exploiting known peptide amphiphile technologies that promote healthy tissue regeneration. (55) In sum, Applicants have demonstrated an improvement upon current peptide-amphiphile technologies through the empirical design of peptides with engineered conformational changes that influence metal cofactor active sites resulting in controlled, protein-like, peptide materials.

Example 2

In Vivo Analysis of Peptide Function

The peptide amphiphiles prepared according to Example 1 are tested for efficacy and their pharmacokinetic profile in the murine models along the lines described in (58) (an anti-tumor model), (59) (an anti-inflammatory model), or (60) (an angiogenesis model).

What is claimed is:

1. A peptide amphiphile according to the formula:

$$c16\text{-}xHy_3z_3$$

wherein:
x = His, Met, Thr, Phe, Asn, Asp, Cys, or Leu;
y = Ala, Val, Leu, Ile, Phe, or Trp;
z = Lys, Glu, or Gly;
c16 = palmitoyl moiety at the N-terminus operatively linked to a biorecognition site or epitope.

2. The peptide amphiphile of claim 1, operatively linked to a heparin binding domain, LRKKLGKA (SEQ ID NO: 2).

3. The peptide amphiphile of claim 1, wherein the biorecognition site or epitope is selected from the group consisting of cell adhesion epitopes, RGD(s) (SEQ ID NO: 10) or IKVAV (SEQ ID NO: 1).

4. The peptide amphiphile of claim 1, wherein x is His, y is Leu, and z is Lys.

5. The peptide amphiphile of claim 1 having a formula selected from the group consisting of c16-HHL$_3$K$_3$—CO$_2$H (SEQ ID NO: 4), and c16-MHL$_3$K$_3$—CO$_2$H (SEQ ID NO: 5).

6. A composition for binding heme comprising:
a plurality of the peptide amphiphiles, each of the plurality of peptide amphiphiles having a polar head group operatively linked with a structural region, which is operatively linked with a heme binding region, operatively linked is bonded with a non-polar tail; and
the plurality of peptide amphiphiles disposed in a pharmaceutically acceptable carrier, wherein the plurality of amphiphiles assemble to form nanofibers, wherein each of the plurality of the peptide amphiphiles comprises:

the formula c16-Hy$_3$z$_3$ wherein:
x = His, Met, Thr, Phe, Asn, Asp, Cys, or Leu,
y = Ala, Val, Leu, Ile, Phe, or Trp,
z = Lys, Glu, or Gly, and
c16 = palmitoyl moiety at the N-terminus.

7. The composition of claim 6, wherein the polar head group is a heparin binding domain.

8. The composition of claim 7, wherein the heparin binding domain has a sequence of LRKKLGKA (SEQ ID NO: 2).

9. The composition of claim 6, wherein the polar head group is selected from the group consisting of cell adhesion epitopes, RGD(s) (SEQ ID NO: 10) or IKVAV (SEQ ID NO: 1).

10. The composition of claim 6, wherein x is His, y is Leu, and z is Lys.

11. The composition of claim 6 having a formula selected from the group consisting of c16-HHL$_3$K$_3$—CO$_2$H (SEQ ID NO: 4), and c16-NHL$_3$K$_3$—CO$_2$H (SEQ ID NO: 5).

12. The composition of claim 6, wherein the pharmaceutically acceptable carrier is sterile water.

13. A method of treating a disease, disorder, or condition associate with an anti-inflammatory mechanism comprising administering the composition of claim 6.

14. The method of claim 13, wherein the disease, disorder, or condition is cardiovascular disease.

15. The method of claim 13, further comprising binding heme to the heme binding region.

16. The method of claim 15, further comprising sequestering the bound heme within the nano fibers.

17. The method of claim 16, further comprising decomposing the bound heme within the nanofibers.

* * * * *